US011116917B2

(12) United States Patent
Houzego et al.

(10) Patent No.: US 11,116,917 B2
(45) Date of Patent: Sep. 14, 2021

(54) DISPENSING DEVICE

(71) Applicant: PFIZER LIMITED, Sandwich (GB)

(72) Inventors: Peter J. Houzego, Cambridge (GB); John Kelshaw Conway, Cambridge (GB); Martin Douglas Pearl, Cambridgeshire (GB); Andrew Mark Bryant, Cambridgeshire (GB)

(73) Assignee: PFIZER LIMITED, Sandwich (GB)

( * ) Notice: Subject to any disclaimer, the term of this patent is extended or adjusted under 35 U.S.C. 154(b) by 370 days.

(21) Appl. No.: 16/183,364

(22) Filed: Nov. 7, 2018

(65) Prior Publication Data

US 2019/0070373 A1 Mar. 7, 2019

Related U.S. Application Data

(63) Continuation of application No. 15/180,634, filed on Jun. 13, 2016, now Pat. No. 10,124,130, which is a
(Continued)

(30) Foreign Application Priority Data

Jul. 2, 2003 (GB) .................................... 0315509

(51) Int. Cl.
*A61M 15/00* (2006.01)
*G06M 1/24* (2006.01)
(Continued)

(52) U.S. Cl.
CPC .... *A61M 15/0073* (2014.02); *A61M 15/0021* (2014.02); *A61M 15/0026* (2014.02);
(Continued)

(58) Field of Classification Search
CPC .......... A61M 15/0001; A61M 15/0003; A61M 15/0045; A61M 15/0046; A61M 15/0048;
(Continued)

(56) References Cited

U.S. PATENT DOCUMENTS 3,818,689 A 6/1974 Muller
4,317,385 A 3/1982 Harvey et al. .................. 74/436
(Continued)

FOREIGN PATENT DOCUMENTS

DE 33 48 370 C 10/2001
DE 3348370 10/2001
(Continued)

OTHER PUBLICATIONS

"International Search Report for PCT/GB2004/002748 dated Jan. 28, 2005".
(Continued)

*Primary Examiner* — Valerie L Woodward
(74) *Attorney, Agent, or Firm* — Sorell, Lenna & Schmidt LLP

(57) ABSTRACT

A device for dispensing individual doses of powder from respective pockets of a disc-shaped carrier by outwardly rupturing a lidding foil by means of pressure on an opposite side surface, the device providing individual respective deaggregation flow paths for each pocket, split airstreams allowing improved entrainment of powder, a cam mechanism for outwardly rupturing the pockets, an indexing mechanism linked to the cam mechanism and a dose counter.

53 Claims, 20 Drawing Sheets

Related U.S. Application Data continuation of application No. 14/461,891, filed on Aug. 18, 2014, now Pat. No. 9,399,103, which is a continuation of application No. 13/560,314, filed on Jul. 27, 2012, now Pat. No. 8,851,070, which is a continuation of application No. 12/795,206, filed on Jun. 7, 2010, now Pat. No. 8,256,416, which is a continuation of application No. 10/565,064, filed as application No. PCT/GB2004/002748 on Jun. 25, 2004, now Pat. No. 8,181,645.

(51) Int. Cl.
  *B65D 83/06* (2006.01)
  *B65D 83/04* (2006.01)

(52) U.S. Cl.
  CPC .... *A61M 15/0031* (2014.02); *A61M 15/0045* (2013.01); *A61M 15/0048* (2014.02); *A61M 15/0058* (2014.02); *A61M 15/0061* (2014.02); *A61M 15/0068* (2014.02); *A61M 15/0075* (2014.02); *B65D 83/06* (2013.01); *G06M 1/248* (2013.01); *A61M 2202/064* (2013.01); *B65D 83/0445* (2013.01)

(58) Field of Classification Search
  CPC ............ A61M 15/005; A61M 15/0051; A61M 15/0053; A61M 15/0055; A61M 15/0058; A61M 15/006; A61M 15/0061; A61M 15/0063; A61M 15/0065; A61M 15/0068; A61M 15/007; A61M 15/0071; A61M 15/0073; A61M 15/0075; A61J 7/0076; A61J 7/02; B65D 83/04; B65D 83/0445; B65D 83/0454
  See application file for complete search history.

(56) References Cited

U.S. PATENT DOCUMENTS

| | | | |
|---|---|---|---|
| 4,627,432 A | 12/1986 | Newell et al. | 128/203.15 |
| 4,811,731 A | 3/1989 | Newell et al. | |
| 5,239,993 A | 8/1993 | Evans et al. | |
| 5,301,666 A | 4/1994 | Lerk et al. | |
| 5,388,572 A | 2/1995 | Mulhauser et al. | |
| 5,437,270 A * | 8/1995 | Braithwaite | A61M 15/0075 |
| | | | 128/203.15 |
| 5,657,748 A | 8/1997 | Braithwaite | |
| 5,657,749 A | 8/1997 | Cox | |
| 5,687,710 A | 11/1997 | Ambrosio et al. | |
| 6,076,521 A * | 6/2000 | Lindahl | A61M 15/0065 |
| | | | 128/203.15 |
| 6,082,356 A * | 7/2000 | Stradella | A61J 1/035 |
| | | | 128/203.12 |
| 6,116,238 A | 9/2000 | Jackson et al. | 128/203.15 |
| 6,182,655 B1 | 2/2001 | Eggimann et al. | |
| 6,520,179 B1 | 2/2003 | Von Schuckmann et al. | |
| | | | 128/203.15 |
| 6,591,832 B1 | 7/2003 | De Jonge et al. | |
| 6,659,307 B1 | 12/2003 | Stradella | |
| 6,679,254 B1 | 1/2004 | Rand et al. | 128/203.15 |
| 6,889,690 B2 | 5/2005 | Crowder et al. | 128/203.15 |
| 7,093,594 B2 | 8/2006 | Harrison et al. | 128/203.15 |
| 7,401,713 B2 | 7/2008 | Ede et al. | |
| 8,181,645 B2 * | 5/2012 | Houzego | A61M 15/0068 |
| | | | 128/203.15 |
| 8,256,416 B2 * | 9/2012 | Houzego | A61M 15/0075 |
| | | | 128/203.15 |
| 8,851,070 B2 | 10/2014 | Houzego et al. | |
| 9,399,103 B2 * | 7/2016 | Houzego | A61M 15/0073 |
| 10,124,130 B2 * | 11/2018 | Houzego | A61M 15/0026 |
| 2002/0033176 A1 | 3/2002 | Casper et al. | |
| 2002/0047021 A1 * | 4/2002 | Blacker | G06M 1/041 |
| | | | 222/23 |
| 2003/0183229 A1 | 10/2003 | Smith et al. | 128/203.12 |
| 2004/0255935 A1 * | 12/2004 | Bruna | A61M 15/009 |
| | | | 128/200.23 |
| 2007/0062525 A1 * | 3/2007 | Bonney | A61M 15/0051 |
| | | | 128/203.21 |
| 2011/0067695 A1 | 3/2011 | Minshull et al. | |

FOREIGN PATENT DOCUMENTS

| | | | |
|---|---|---|---|
| DE | 3348370 C | 10/2001 | |
| EP | 0211595 A2 | 2/1987 | |
| EP | 0 469 814 A | 2/1992 | |
| EP | 0469814 | 2/1992 | |
| EP | 0469814 A | 2/1992 | |
| EP | 0469814 A1 * | 2/1992 | ........ A61M 15/0031 |
| EP | 0649814 | 10/1994 | ............... B67C 3/24 |
| EP | 1106196 | 6/2001 | |
| EP | 1106196 A | 6/2001 | |
| EP | 1644063 | 4/2006 | |
| EP | 1730676 | 12/2006 | |
| GB | 2 242 134 A | 9/1991 | |
| GB | 2242134 | 9/1991 | |
| GB | 2242134 A | 9/1991 | |
| GB | 0315509.0 | 7/2003 | |
| GB | 0403394.0 | 2/2004 | |
| JP | HE19-504455 | 5/1997 | |
| JP | HEI9-504455 | 5/1997 | |
| JP | 2013508165 | 3/2003 | |
| WO | 95/11715 | 5/1995 | |
| WO | 9511715 | 5/1995 | |
| WO | 9511715 A | 5/1995 | |
| WO | WO 95/11715 A | 5/1995 | |
| WO | WO 9511715 | 5/1995 | |
| WO | 9633759 | 10/1996 | |
| WO | 9633759 A | 10/1996 | |
| WO | WO 96/33759 A | 10/1996 | |
| WO | WO 9633759 | 10/1996 | |
| WO | 9727892 | 8/1997 | |
| WO | WO 9727892 | 8/1997 | ............ A61M 15/00 |
| WO | 99/47199 | 9/1999 | |
| WO | WO 0045879 | 8/2000 | ............ A61M 15/00 |
| WO | 0045879 | 10/2000 | |
| WO | 01/017595 | 3/2001 | |
| WO | 01/17595 A1 | 3/2001 | |
| WO | 0117595 | 3/2001 | |
| WO | 0117595 A | 3/2001 | |
| WO | 01017959 | 3/2001 | |
| WO | WO 01/17595 A | 3/2001 | |
| WO | WO 0117595 | 3/2001 | |
| WO | 200129765 | 4/2001 | |
| WO | 01/031578 A1 | 5/2001 | |
| WO | 0185097 | 11/2001 | |
| WO | 0185097 A | 11/2001 | |
| WO | WO 01/85097 A | 11/2001 | |
| WO | WO 0185097 | 11/2001 | |
| WO | 02/24263 | 3/2002 | |
| WO | 0224263 | 3/2002 | |
| WO | 0224263 A | 3/2002 | |
| WO | WO 02/24263 A | 3/2002 | |
| WO | WO 0224263 | 3/2002 | |
| WO | 02053215 | 7/2002 | |
| WO | WO 02053215 | 7/2002 | ............ A61M 11/00 |
| WO | 03024514 | 9/2002 | |
| WO | 02094357 | 11/2002 | |
| WO | 02094357 A | 11/2002 | |
| WO | WO 02/094357 A | 11/2002 | |
| WO | WO 02094357 | 11/2002 | |
| WO | 02/102444 A1 | 12/2002 | |
| WO | 03015857 | 2/2003 | |
| WO | 03015857 A | 2/2003 | |
| WO | WO 03/015857 A | 2/2003 | |
| WO | WO 03015857 | 2/2003 | |
| WO | 03/024514 | 3/2003 | |
| WO | 03024514 | 3/2003 | |
| WO | 03024514 A | 3/2003 | |
| WO | WO 03/024514 A | 3/2003 | |
| WO | WO 03024514 | 3/2003 | |
| WO | 03/028792 A1 | 4/2003 | |
| WO | 03/035137 A2 | 5/2003 | |

(56) References Cited

FOREIGN PATENT DOCUMENTS

| WO | 2003061743 | 7/2003 |
|---|---|---|
| WO | 03/084502 A1 | 10/2003 |
| WO | 2005079727 A2 | 9/2005 |

OTHER PUBLICATIONS

"Brazilian Office Action dated Nov. 12, 2015 for BR Application No. BR 122015016053-7".

"Non-Final Office Action for Brazilian Patent Application No. PI0412122-8 dated May 6, 2015".

"First Office Action for Japanese Application No. 2014-087001 dated Feb. 16, 2015".

"Norwegian Search Report for Norwegian Application No. 20060299 dated Oct. 13, 2014".

"Non-final Office Action for Brazilan Patent Application No. PI0412122-8 dated May 6, 2015".

Bickford, John H., "Geneva Mechanisms," Mechanisms for Intermittent Motion. Industrial Press Inc. New York, NY, 1972.

Communication of a Notice of Opposition issued by the European Patent Office, dated Jul. 29, 2019, issued in European Application No. 14162934.5, now EP Patent No. 2752216, for Dispensing Device.

Reply to Communication of a Notice of Opposition filed Dec. 27, 2019 in the European Patent Office in European Application No. 14162934.5, now EP Patent No. 2752216, for Dispensing Device.

Summons to attend oral proceedings pursuant to Rule 115(1) EPC dated Jan. 18, 2021 issued by the European Patent Office in corresponding European Application No. 14162934.5 filed Jun. 25, 2004, now EP Patent No. 2752216 to Pfizer Limited, granted Jul. 9, 2014.

Reply to Examination Report in Opposition Proceedings dated Sep. 17, 2020 filed in the European Patent Office in corresponding European Application No. 14162934.5 filed Jun. 25, 2004, now EP Patent No. 2752216 to Pfizer Limited, granted Jul. 9, 2014.

Brief Communication in Opposition Proceedings from the European Patent Office dated Sep. 24, 2020 in corresponding European Application No. 14162934.5 filed Jun. 25, 2004, now EP Patent No. 2752216 to Pfizer Limited, granted Jul. 9, 2014.

Brief Communication in Opposition Proceedings from the European Patent Office dated Sep. 23, 2020 including a Reply to the preliminary opinion of the Opposition Division dated May 7, 2020 filed in corresponding European Application No. 14162934.5 filed Jun. 25, 2004, now EP Patent No. 2752216 to Pfizer Limited, granted Jul. 9, 2014.

Preliminary opinion of the opposition division indicating issue of summons at a later time and shorter notice from the European Patent Office dated May 7, 2020 in corresponding European Application No. 14162934.5 filed Jun. 25, 2004, now EP Patent No. 2752216 to Pfizer Limited, granted Jul. 9, 2014.

Annex to communication in Opposition Proceedings dated Jan. 18, 2021 issued by the European Patent Office in corresponding European Application No. 14162934.5 filed Jun. 25, 2004, now EP Patent No. 2752216 to Pfizer Limited, granted Jul. 9, 2014.

Auxiliary Requests During Opposition dated Sep. 17, 2020 filed in the European Patent Office in corresponding European Application No. 14162934.5 filed Jun. 25, 2004, now EP Patent No. 2752216 to Pfizer Limited, granted Jul. 9, 2014.

Extended European Search Report dated May 12, 2021 issued by the European Patent Office in corresponding European Application No. EP 21 15 2808.

Prime, David, et al. Review of dry powder inhalers. Advanced Drug Delivery Reviews. vol. 26 (1997) pp. 51-58.

Brief Communication from the European Patent Office including Written Submission to the Oral Proceedings by Opponent (Glaxo Group Limited). Opposition in corresponding EP Patent 2752216 for Dispensing Device. Jul. 29, 2021.

Brief Communication from the European Patent Office including Written Submission to the Oral Proceedings by Patentee (Pfizer Ltd.) Opposition in corresponding EP Patent 2752216 for Dispensing Device. Jul. 28, 2021.

Auxiliary Requests 1a and 7a filed in the European Patent Office by Patentee in Opposition in corresponding EP Patent 2752216 for Dispensing Device. Jul. 23, 2021.

Consolidated list of cited opposition documents. Opposition in corresponding EP Patent 2752216 for Dispensing Device. Jul. 23, 2021.

Letter accompanying subsequently filed items. Submission in opposition proceedings made following summons to attend oral proceedings. (Opponent) Opposition in corresponding EP Patent 2752216 for Dispensing Device. Jul. 23, 2021.

Letter accompanying subsequently filed items. Submission in opposition proceedings made following summons to attend oral proceedings. (Patentee) Opposition in corresponding EP Patent 2752216 for Dispensing Device. Jul. 23, 2021.

\* cited by examiner

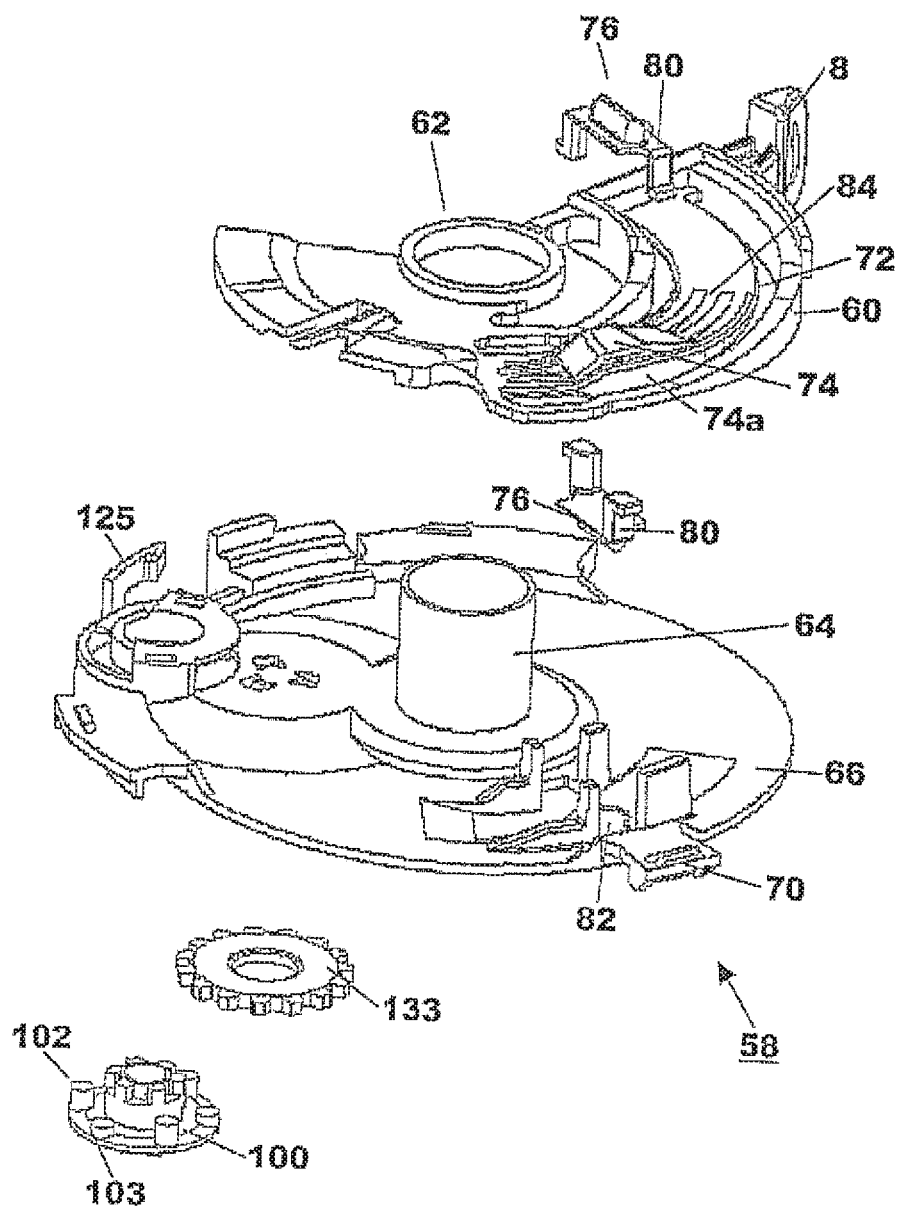

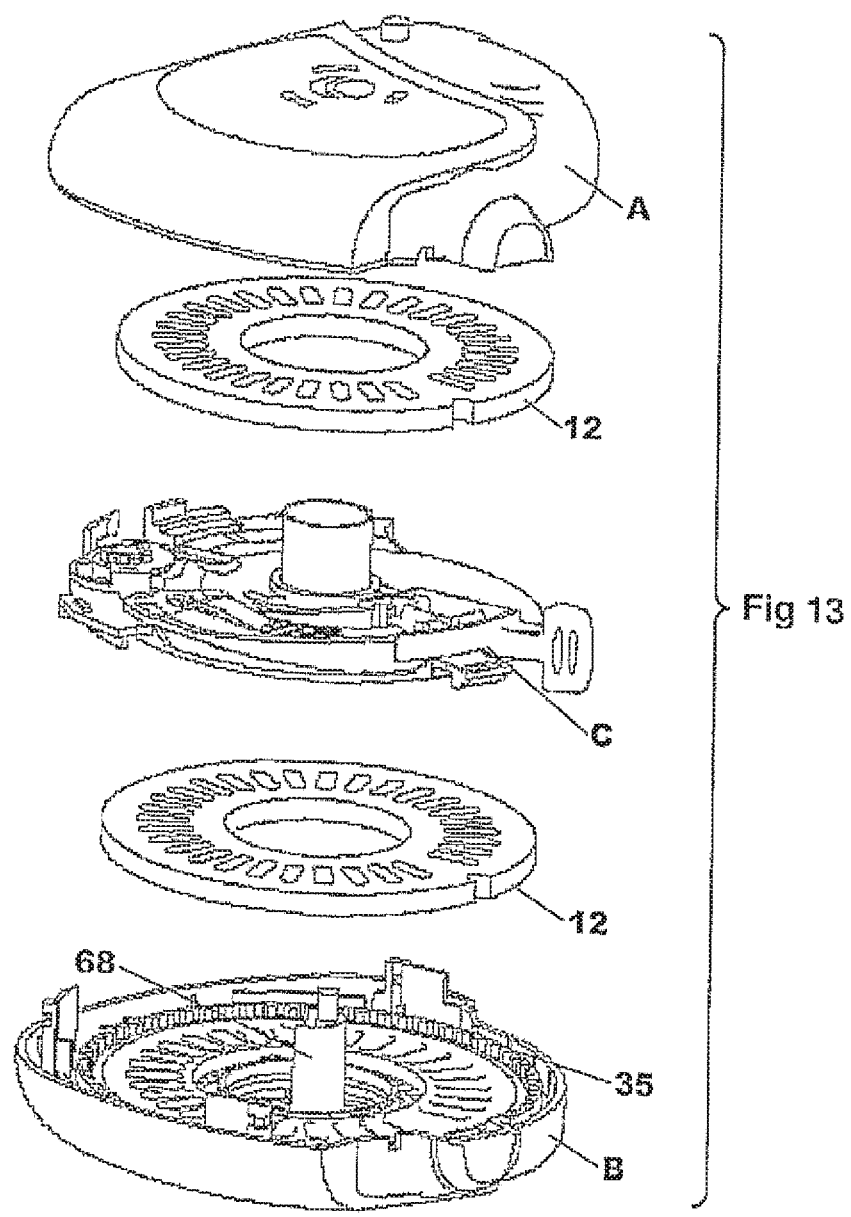

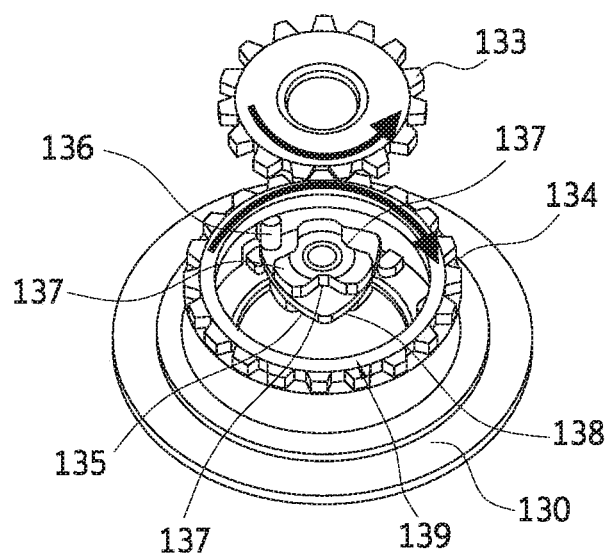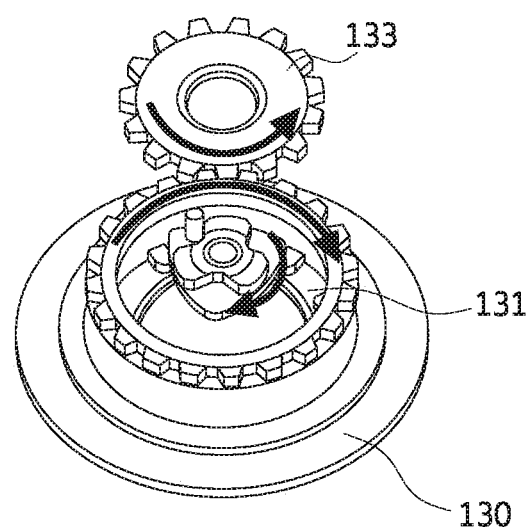
FIG. 19(a)   FIG. 19(b)
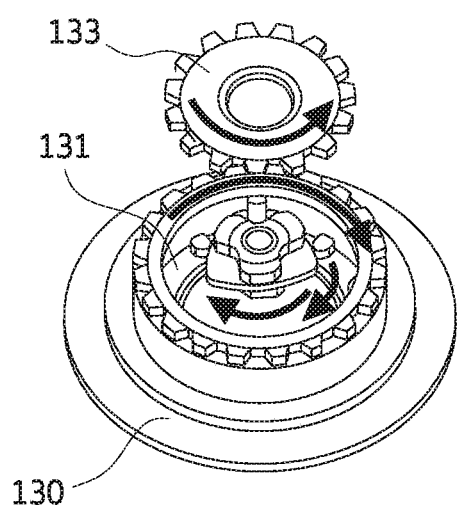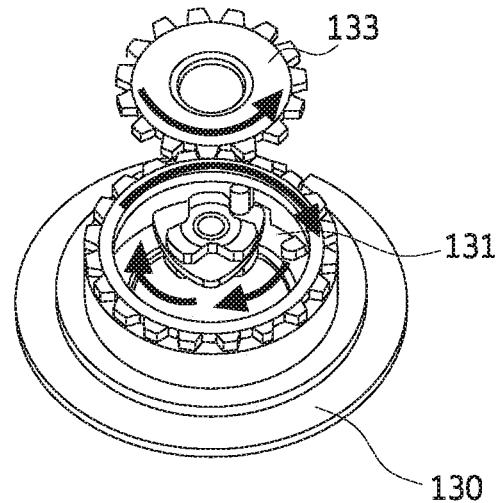
FIG. 19(c)   FIG. 19(d)

DISPENSING DEVICE

This application is a continuation of application Ser. No. 14/461,891, filed Aug. 18, 2014 which is a continuation of application Ser. No. 13/560,314, filed Jul. 27, 2012, now U.S. Pat. No. 8,851,070, issued Oct. 7, 2014, which is a continuation of application Ser. No. 12/795,206, filed Jun. 7, 2010, now U.S. Pat. No. 8,256,416, issued Sep. 4, 2012, which is a continuation of application Ser. No. 10/565,064, filed Jul. 7, 2006, now U.S. Pat. No. 8,181,645, issued May 22, 2012, which claims the benefit of International Patent Application No. PCT/GB2004/002748, filed Jun. 25, 2004, which claims the benefit of Great Britain Patent Application No. 0315509.0, filed Jul. 2, 2003, all of which are incorporated by reference herein in their entireties.

TECHNICAL FIELD

The present invention relates to a dispensing device, in particular for dispensing individual doses of powder from respective pockets of a carrier.

A wide variety of devices are known for dispensing doses of medicament in the form of powder for inhalation. Devices are known which contain a store of powdered medicament from which individual doses are metered as required. Devices are also known which include carriers having a plurality of pockets containing respective doses of powder. These carriers are typically in the form of blister-packs. All of these devices face problems of providing reliable, repeatable and accurate inhaled amounts of powder.

There are problems in ensuring that all of a dispensed dose of powder is entrained into the airstream for inhalation. Furthermore, some of the powder which is originally provided for inhalation may adhere to surfaces within the device. This will reduce the inhaled dose. However, more importantly, after a number of uses, previously adhered powder may become dislodged, thereby resulting in an unwanted and undesirable increase in the inhaled dose. There are other problems in providing repeatable and consistent release of powder into the inhalation airstream as desired.

In attempting to reduce these problems, previous devices suffer problems of increased size, complexity and/or cost.

U.S. Pat. No. 4,811,731 describes an inhaler having a support for a blister pack having an annular array of blisters. The support faces a tray having upstanding walls defining a flow path to a mouthpiece. In use, the support and blister pack is consecutively indexed such that powder from respective blisters is dispensed via the flow path defined by the tray and upstanding walls. Because the same tray and upstanding walls are used for all of the blisters, there is the problem that powder can become adhered to the tray and upstanding walls and then dislodged subsequently.

It is an object of the present invention to overcome or at least reduce these problems.

SUMMARY

According to the present invention, there is provided a device for dispensing individual doses of powder from respective pockets of a carrier, the device including a support for a carrier having a plurality of pockets containing respective doses of powder and a mouthpiece through which to inhale an airstream carrying a dose of powder, the device further including walls for defining individual respective first flow paths downstream of each respective pocket of a supported carrier wherein each individual respective first flow path is defined entirely by respective walls unique to that individual respective first flow path, is for connecting the corresponding respective pocket to the mouthpiece and is for deaggregating powder in the airstream.

In this way, each pocket of powder is provided with its own first flow path such that any powder which does adhere to the walls of that first flow path will not affect subsequent dispensing inhalations through the device. There are no walls in common between respective first flow paths such that powder adhering to walls of a first flow path will not affect subsequent doses. In particular, subsequent inhalations will draw airstreams through the first flow paths of the respective pockets being dispensed such that, even if previously adhered powder is dislodged in the first flow paths of previously dispensed pockets, this powder will not be part of the inhalation airstream and, hence, will not be inhaled by the user.

According to the present invention, there is also provided a device for dispensing individual doses of powder from respective pockets of a carrier, the device including: a support for a carrier having a plurality of pockets containing respective doses of powder, and a mouthpiece through which to inhale an airstream carrying a dose of powder, the device further including: walls for defining individual respective first flow paths downstream of each respective pocket of a supported carrier for connecting the corresponding respective pockets to the mouthpiece and deaggregating powder in the airstream; an arrangement for moving individually each pocket from a respective storage position to a respective discharge position, wherein each pocket, in the respective discharge position, forms an integral part of the individual respective first flow path.

Preferably, the device is for use with a carrier having pockets provided with a lidding sheet, the device allowing the lidding sheet to be ruptured as a consequence of moving a pocket from a respective storage position to a respective discharge position.

Preferably, the device further includes walls defining a second flow path connecting with the mouthpiece and bypassing the pockets.

This allows an increase in flow volume through the device and a reduction in the resistance to flow, such that a user may more easily inhale through the device. This is most important where the size of the pockets is not sufficient to allow the flow volume to reach that necessary to carry medicament into the lung. Furthermore, it also becomes possible to entrain powder in the airstream over a small, but sustained, period of time, rather than substantially all at once. The powder may be entrained during a mid-portion of inhalation, thereby improving the transfer of powder to the user. The device should preferably provide similar performance over flow rates ranging from 28.3 l/min to 60 l/min and should preferably have a pressure drop not exceeding 4 kPa at 60 l/min.

Preferably, with the device configured to dispense a dose of powder from one of the pockets of the supported carrier, the respective flow path connects with the second flow path downstream of the bypass and at an angle such that substantially no powder impacts with the walls defining the second flow path. Some impact could be allowed, but then preferably substantially no deposition occurs. Some powder could be allowed to be deposited on the walls defining the second flow path, but then preferably, with repeated use of the device and the second flow path, no more than 25% or preferably no more than 15% of a dose remains deposited on the walls defining the second flow path. It will be appreciated that the airstream through the second flow path also acts to scour or scavenge powder deposited on the walls defining the second flow path.

In other words, it is thus possible for a part of the second flow path to be used consecutively for all of the pockets of the carrier. However, since the respective first flow paths provide the required deaggregation, the second flow path can be arranged to provide a minimum amount of turbulence and to avoid substantially any powder adhering to its walls. By providing an appropriate angle at which the first flow paths meet the second flow path, powder can substantially be prevented from impacting the walls of the second flow path when it joins the second flow path from the respective first flow path.

Preferably, where the respective first flow path connects with the second flow path, the angle is less than 45 degrees, more preferably less than 30 degrees.

This ensures that substantially no powder adheres to the walls defining the second flow path.

Preferably, the support for the carrier and the walls defining the first flow path are moveable with a supported carrier so as to selectively connect respective first flow paths with the second flow path and, hence, selectively dispense doses of powder from respective pockets of the supported carrier.

In this way, the device can be provided with a single mouthpiece and dispensing mechanism so as to minimise cost and complexity and yet still provide each pocket of the carrier with its own respective first flow path in which deaggregation and any adherence of powder occurs.

In a preferred embodiment, the carriers are disc-shaped with a circumferential array of pockets. In this embodiment, the pockets and their respective first flow paths are indexed by rotation relative to the second flow path and mouthpiece so as to dispense consecutively doses of powder for inhalation through the mouthpiece.

Preferably, the walls defining the first flow paths include, upstream of the pockets, respective portions of relatively reduced cross-sectional area orientated so as to be directed towards respective pockets and direct a relatively high velocity airstream into the respective pockets.

Indeed, according to the present invention, there is also provided a device for dispensing a dose of powder from a pocket of a carrier, the device including a support for a carrier having a pocket containing a dose of powder and a mouthpiece through which to inhale an airstream carrying a dose of powder, the device further including walls defining first and second flow paths connecting with the mouthpiece, the first flow path connecting the pocket of the supported carrier to the mouthpiece and the second flow path bypassing the pocket, wherein the walls defining the first flow path include, upstream of the pocket, a portion of relatively reduced cross-sectional area orientated so as to be directed towards the pocket and direct a relatively high velocity airstream into the pocket.

In this way, the high velocity airstream can erode the powder in the pocket so as to progressively entrain it into the airstream, rather than merely attempt to flush the powder from the pocket. This results in the powder being entrained into the airstream over a sustained period of time. The time is preferably within the range of 0.01 s to 1.0 s and more preferably in the range of 0.2 s to 0.5 s. This provides improved inhalation characteristics.

Furthermore, by virtue of the second flow path in conjunction with the first flow path, resistance to airflow can be reduced and volume of airflow increased. The portions of relatively reduced cross-sectional area produce a small high velocity stream suitable for eroding the powder. By providing these in conjunction with the second flow path, the user is still able to inhale relatively easily through the device, despite the restriction of the respective reduced cross-sectional area portions.

As will be appreciated, this arrangement has similar advantages when used with a carrier having only a single pocket and, hence, only a single first flow path.

Preferably, each portion has a cross-sectional area between 50% and 66% of the cross-sectional area of the smallest part of the second flow path. Indeed, preferably, the cross-sectional areas of the non-reduced cross-section parts of each flow path are provided between 110% and 150% of the minimum values in their own path order to maintain the high air velocities required to keep the powder entrained without contributing significantly to pressure drop.

This allows a suitably high velocity airstream to be directed into a pocket without unduly increasing the overall resistance to inhalation and allowing a sufficiently high overall volume of airflow.

In the preferred embodiment, there is another second flow path for the other side of the device and its corresponding carrier. In use, a patient inhales through both second flow paths whilst drawing powder from the first flow path in use. Each of the second flow paths is expected to carry approximately 40%> of the total inhaled air for an average use.

Actual requirements will vary depending upon the nature of the powder and the intended user. For an easily dispensed powder, the portion forming the inlet to the pocket can be small and, for a child or patient with COPD (Chronic Obstructive Pulmonary Disease), the total pressure drop should be low. In this case, an inlet portion could be provided with a cross-sectional area of 2 $mm^2$ and a bypass second flow path with a minimum cross-sectional area of 8 $mm^2$, resulting in a ratio of 25%. On the other hand, with sticky powder for a healthy adult, the inlet portion could be provided with a cross-sectional area of 4 $mm^2$ together with a bypass second flow path having a minimum cross-sectional area of 6 $mm^2$, resulting in a ratio of 66%. Of course, intermediate values are also possible and a preferred arrangement has an inlet portion of approximately 3 $mm^2$ with a second flow path minimum cross-sectional area of 6 $mm^2$, resulting in a ratio of 50%.

Referring to FIG. 21(a) of the accompanying drawings, it will be noted that it is important for the cross sectional areas $A_1$, $A_2$ and $A_3$ to be between 120% and 200% of the smallest cross sectional area B for the bypass flow. Similarly the cross sectional areas $C_1$, $C_2$ and $C_3$ should be between 120% and 200%) of the smallest cross-sectional area of the portions D for the flow path through a pocket. The combined flow path cross sectional area E should then be greater than $A_3$ plus $C_3$ such that air velocity in the pocket is not reduced.

For this arrangement, the pressures at $A_3$, $C_3$, and E can all be the same and equal to or less than that in the mouth of the patient. The whole pressure drop due to inhalation then occurs across both B and D. For cohesive formulations, it is advantageous to have the maximum air velocity through the pocket portion. This may be achieved by minimizing the pressure at $C_3$ during inhalation. If the mouthpiece is shaped to cause the air to expand with laminar flow by the use of a small divergence angle, typically less than 10 degrees, then it is possible to cause the pressure at $C_3$ to be below the pressure in the mouth, thus increasing the air velocity through the pocket portion.

The ratio of B to D sets the ratio of air flowing through the bypass and the pocket.

The sum of the areas B and D sets the overall flow resistance and is preferably set to give 3 kPa to 4 kPa at 60 J/m.

For the preferred embodiment, storing individual doses of powder of approximately 20 mg in pockets having volumes of approximately 30 mm$^3$, each portion preferably has a cross-sectional area of between 2.0 mm$^2$ and 10.0 mm$^2$, more preferably between 2.0 mm$^2$ and 5.0 mm$^2$.

The reduced cross-section is selected to be between 50%> and 90% of the area which, for the normal range of inhalation rates and volumes, provides a suitable high velocity airstream into the pocket.

FIG. 21(b) of the accompanying drawings illustrates the preferred cross sections for a particular embodiment. In particular, the minimum cross sectional area B for the bypass flow is approximately 5.0 mm$^2$, the minimum cross sectional area D for the pocket flow is approximately 3.8 mm2 and the combined flow path cross sectional area E is approximately 12.0 mm$^2$.

According to the present invention, there is also provided a device for dispensing individual doses of powder from respective pockets of a pair of carriers, the device including a support for two disc-shaped carriers, each disc-shaped carrier having at least one substantially planar first side surface having an annular array of cavities in which respective pockets are formed and a respective first lidding sheet sealed to the first side surface for enclosing the cavities wherein the support is for rotatably supporting the carriers about a substantially common axis, a mouthpiece through which to inhale an airstream carrying powder from the carriers, a dispensing mechanism for releasing into the airstream the powder of a respective pocket of a supported carrier and an indexing mechanism for rotating the carrier relative to the dispensing mechanism so as to enable powder to be released from different pockets.

This arrangement provides an extremely compact and efficient way of holding and dispensing a plurality of pockets of powder. A single dispensing mechanism can be provided for both carriers and the carriers may easily be moved so as to selectively bring each of their pockets in line with the dispensing mechanism and an airstream for carrying powder to the mouthpiece.

The arrangement can be used in conjunction with the features described above and is particularly effective in this regard.

Preferably, between consecutive dispensing of powder from one of said carriers, the indexing mechanism is operable to rotate both of said carriers relative to the dispensing mechanism.

In other words, where powder is dispensed from a first disc, powder will also be dispensed from the second disc before more powder is dispensed from the first disc. Hence, similarly, preferably, between consecutive dispensing of powder from the other of said carriers, the indexing mechanism is operable to rotate both of said carriers relative to the dispensing mechanism.

Preferably, the dispensing mechanism is operable to release powder from a pocket of each carrier for a single inhalation of both respective powders simultaneously.

In other words, powder is dispensed from the pocket of a first disc and also powder is dispensed from a pocket of a second disc. The user may then inhale the powder dispensed from both discs simultaneously. This allows two different medicaments to be administered simultaneously without the medicaments coming into contact until immediately before or indeed during the inhalation process.

Preferably, the mechanism is operable to dispense medicament from a pocket of each disc simultaneously.

Hence, having rotated the discs to an appropriate position with an unopened pocket of each disc available, the mechanism then opens both pockets together in one operation.

Alternatively, the dispensing mechanism may be operable to release powder from a pocket of one of the carriers for inhalation then to release powder from a pocket of the other of the carriers for inhalation.

In this way, a user may administer two different pharmaceuticals immediately one after the other or may use the inhalation device as part of a course of treatment whereby different medicaments are administered alternately after predetermined periods of time. By way of example, a steroid compound could be dispensed from one disk and a long acting beta-agonist from the other disk for the treatment of e.g. asthma or chronic obstructive pulmonary disease: Examples of long acting beta-agonists include formoterol and salmeterol and examples of steroids include fluticasone propionate, budesonide and monetasone furoate.

Indeed, the inhalation device could include three or more discs such that more complicated courses of pharmaceuticals could be administered. Indeed, the mechanism could be arranged so as to dispense a predetermined number of doses from one disc before administering a dose from the other disc.

In certain embodiments, the mechanism may be operable to release powder from a pocket of one carrier and from a pocket of the other carrier consecutively.

Such a system could be used when the powder of the two pockets is inhaled together or consecutively.

A device may be provided with two of said disc shaped carriers respectively containing powder of different medicaments.

This allows, as mentioned above, different medicaments to be dispensed from the same device.

Preferably, between consecutive dispensing of powder, the indexing mechanism is operable to rotate one of said carriers in turn between consecutive dispensing positions before rotating the other of said carriers.

In other words, the indexing mechanism is arranged to move one of the carriers between consecutive pockets whilst the other carrier remains where it is.

The dispensing mechanism and the indexing mechanism may together be operable to dispense powder from all of the pockets from one of the said carriers before dispensing powder from pockets of the other of said carriers.

This allows the use of an indexing mechanism which always moves one or other of the carriers onto its next position.

According to the present invention, there is also provided a device for dispensing individual doses of powder from respective pockets of carrier, the device including a first support for a first carrier having first and second side surfaces opposite each other, an array of cavities in which respective pockets are formed and a first lidding sheet sealed to the first side surface, a first prodger member moveable towards and away from the second side surface of a supported first carrier between a retracted and an extended position and a cam member adjacent to and moveable generally parallel with the second side surface of a supported carrier between a rest position and a primed position, wherein the cam member has a first cam surface for engaging with the first prodger member such that movement of the cam member from the rest position to the primed position moves the prodger member from the retracted position to the extended position so as to press upon the second side surface of a supported first carrier and outwardly rupture the first lidding sheet of the supported first carrier.

In this way, a compact and effective mechanism is provided for opening individual pockets of a carrier. The cam member may be provided with a relatively large amount of movement, but, since this is generally parallel to the plane of the carrier, this need not take up excessive space. At the same time, converting this large amount of movement to only the small amount of movement required for the prodger member, the user is given a large mechanical advantage such that dispensing of the powder from a pocket is relatively easy and well controlled.

Preferably, the device further includes a second support for a second carrier having first and second side surfaces opposite each other, an array of cavities in which respective pockets are formed and a first lidding sheet sealed to the first side surface, the first and second carriers being supported with respective second side surfaces facing each other, a second prodger member moveable towards and away from the second side surface of a supported second carrier between a retracted and an extended position, wherein the cam member has a second cam surface for engaging with the second prodger member such that movement of the cam member from the rest position to the primed position moves the prodger member from the retracted position to the extended position so as to press upon the second side surface of a supported second carrier and outwardly rupture the first lidding sheet of the supported second carrier.

In this way, the same advantages are achieved for a second carrier. Furthermore, these advantages are achieved using only a single cam member for dispensing from both of the two carriers. Hence, the device is very efficient in its use of space.

The device may be arranged as described above so as to achieve the same advantages. Thus, preferably, the device further includes an indexing mechanism for moving the first and second supports relative to the first and second prodger members so as to selectively align pockets of the carrier with respective prodger members.

In this way, the carriers are efficiently moved and located with respect to the dispensing mechanism and the mouthpiece.

Preferably, the indexing mechanism is arranged such that, with one of the first and second prodger members aligned with a respective pocket, the other of the first and second prodger members is aligned between respective pockets, whereby movement of the cam member from the rest position to the primed position causes only one of the first and second prodger members to outwardly rupture the first lidding sheet of the corresponding one of the first and second carriers.

In this way, although the cam member is moved in the same way for each use, the indexing mechanism positions the carriers such that the pocket of one carrier is dispensed for a particular use of the cam member. Nevertheless, the same cam member is still able to open pockets from either of the carriers. Again, this is a highly efficient use of the mechanism and also of space within the device.

Preferably, the cam member is moveable in a direction towards and away from the second side surfaces of the supported first and second carriers such that, when the other of the first and second prodger members is aligned between respective pockets, movement of the cam member from the rest position to the primed position and the resulting engagement with the other of the first and second prodger members with the corresponding cam surface causes the other of the first and second prodger members to abut the corresponding second side surface and the cam member to be moved towards the corresponding one of the first and second carriers.

Thus, for each use of the cam member, each cam surface pushes against a corresponding cam member. However, since one-prodger member will abut a second side surface between pockets and, therefore, will not itself move, the corresponding cam surface would actually cause the cam member to move away from that second side surface.

In this way, in effect, both cam surfaces contribute to movement of a prodger member to open a pocket, such that each cam surface need have only a relatively small slope.

Preferably the cam member is provided on a priming member moveable as part of the indexing mechanism.

In this way, it is not necessary for a user to operate two separate actuators. Actuating the device to move the cam member in one direction will prime the device so as to dispense a dose of powder for inhalation and then the movement of the cam member back to its rest position will index at least one of the carriers ready for another pocket of powder to be dispensed.

Preferably, the indexing mechanism is arranged such that, after the first and second carriers have been indexed past all of their respective pockets, the first and second prodger members are both aligned between pockets of respective carriers and, hence, provide resistance to movement of the cam member.

This provides a feature of "lock-out" whereby once all of the pockets of the carriers have been used and the device is effectively empty, the user is provided with a physical feedback. In particular, it becomes difficult for the user to move the priming lever of the device, since the cam member is unable to move the prodger members.

Preferably, the cam member includes an elongate flexible member having first and second cam surfaces on opposite respective sides.

In this way, when it is required for the cam member or a portion of it to move from side to side, it is sufficient for only the elongate flexible member to move.

Preferably, the first cam surface and/or the second cam surface includes at least one groove into which any stray powder from previously dispensed pockets may move.

In this way, stray powder will not interfere with the interface between the cam surfaces and the prodger members such that operation will not be impeded.

Preferably, the device is for use with carriers having the cavities formed from respective through holes between the first and second side surfaces, having second lidding sheets sealed to the second side surfaces and having respective cup shaped inserts in each cavity orientated with open portions facing the first lidding sheets, wherein the first prodger member and/or second prodger member is arranged to penetrate an aligned through hole through a second lidding sheet so as to push the corresponding second insert outwardly through the first lidding sheet.

This is a particularly effective way of dispensing doses of powder and the mechanism for moving the prodgers is particularly effective in pushing the inserts as required.

Preferably, at least one of the cam surfaces is resiliently deformable, the cam member being dimensioned so as to move the prodger members beyond the extended position such that, once a prodger member reaches its respective extended position, further movement of the cam member causes the at least one of the cam surfaces to resiliently deform.

In this way, the device can itself compensate for variations in tolerances and it is not necessary for the cam member to move the prodger members by exactly the distance required.

Preferably, each support includes a peripheral array of gear teeth and the indexing mechanism is engageable with the gear teeth so as selectively to move the supports and carriers.

This provides an advantageous way of moving and controlling the positions of the carriers.

Preferably, the indexing mechanism includes a priming member mounted for rotation about a central axis and a Geneva wheel rotatably mounted on an axis offset from the central axis for interaction with the priming member and gear teeth of the supports such that rotation of the priming member from a first position to a second position causes rotation of at least one of the supports by a predetermined angle and rotation of the priming member back from the second position to the first position causes no rotation of at least one of the supports.

Indeed, according to the present invention, there is also provided a device for dispensing individual doses of powder from respective pockets of a carrier, the device including a chassis, a first support mounted on the chassis for rotation about a central axis and for supporting a first carrier having cavities with respective pockets formed therein and arranged in a circular array centred on the central axis, the first support including an array of gear teeth centred on the central axis, a priming member mounted on the chassis for rotation about the central axis and an intermittent-motion mechanism mounted on the chassis for interaction with the priming member and gear teeth of the first support such that rotation of the priming member from a first position to a second position causes rotation of the first support by a predetermined angle and rotation of the priming member back from the second position to the first position causes no rotation of the first support.

This allows a user to move the priming member through a relatively large and imprecise range of movements whilst ensuring that the support and carrier is moved by a predetermined amount.

Preferably, the intermittent-motion mechanism is a Geneva wheel rotatably mounted on the chassis on an axis offset from the central axis.

The device may further include a second support mounted on the chassis for rotation about the central axis and for supporting a second carrier having cavities with respective pockets formed therein and arranged in a circular array centred on the central axis, the second support including an array of gear teeth centred on the central axis wherein the Geneva wheel may interact with the gear teeth of the second support such that rotation of the priming member from the first position to the second position causes rotation of the second support by a predetermined angle and rotation of the priming member back from the second position to the first position causes no rotation of the second support.

In this way, the priming member may be used to rotate both the first and second supports and their associated carriers.

Preferably, the respective arrays of gear teeth of the first and second supports are incomplete circular arrays leaving respective spaces such that, with a space positioned between the Geneva wheel, rotation of the priming member will not rotate the respective supports.

In this way, it is possible for the priming member to rotate selectively one or other of the supports.

The indexing mechanism may be actuated by a lever pivoted about the disc axis being moved through an angle between 30° and 180° and preferably the indexing movement remains constant provided that the lever moves through a minimum angle.

The mechanism preferably locates to a radial accuracy sufficient to ensure that the prodger member accurately locates on the pocket. Preferably, the force required to index the motion is between 1 N and 20 N.

Preferably, the indexing mechanism holds the carriers in place so that they will not move when subjected to shocks such as experienced when carried in the pocket or dropped onto a hard surface. It can be designed to index precisely between whatever number of pockets are on a disc.

The indexing mechanism preferably causes the selected disc carrier to increment through a fixed angle to a deferred location so that the airway of the pocket that will be opened next is aligned to the airway leading to the mouthpiece.

It is preferable that the priming lever used for indexing is not rigidly linked to the position of the disc, as this would cause any small movement of the lever to disturb the alignment of the airways. Hence it is preferable that the correct motion of the disc occurs as the lever moves through the central part of its travel and that its start and end positions are not critical to accurate operation.

Although various mechanisms could be used to achieve this type of motion, the preferred approach is to use a Geneva mechanism to allow the lost motion aspect of the indexing. A combination of gears with the Geneva mechanism can ensure that for every operation of the priming lever the carrier disc indexes a predetermined angle. For example, a carrier disc that has 31 positions would require an indexing angle of 11.61 degrees.

Preferably, the device further includes a changeover component located between the first and second supports, the first support having a first feature engaging with the changeover component and the second support having a second feature for engaging with the changeover component, wherein with the space of the second support adjacent the Geneva wheel, consecutive rotations of the priming member cause only the first support to rotate until the first feature engages the changeover component and then to move the changeover component so as to engage with the second feature and rotate the second support to a position with the space of the second support not adjacent the Geneva wheel, the space of the first support then being adjacent the Geneva wheel and consecutive rotations of the priming member causing only the second support to rotate.

In this way, it is possible to continuously operate the priming member and yet achieve automatic changeover between indexing of the first support and then the second support.

Preferably, the changeover component is arranged such that, when the priming member rotates the second support back around to the position with the space of the second support adjacent the Geneva wheel, the second feature does not engage with the changeover component and consecutive rotations of the priming member cause no rotation of either support.

In this way, the device is automatically prevented from indexing to previously used pockets of the carriers.

At this point in the operation, as described above, the first and second prodger members are preferably both aligned between pockets of respective carriers and, hence, provide resistance to movement of the cam member. This provides the feature of "lock-out".

According to the present invention, there is also provided a device for dispensing individual doses of powder from respective pockets of a carrier, the device including first and second supports rotatable about a central axis and for supporting respective first and second carriers having cavities with respective pockets formed therein and arranged in respective first and second circular arrays centred on the central axis, a changeover component located between the first and second supports, the first support having a first feature for engaging with the changeover component and a second component having a second feature for engaging with the changeover component and an indexing mechanism arranged to rotate each of the first and second supports, wherein the indexing mechanism is arranged to rotate the first support until the first feature engages the changeover component such that the first support then moves the changeover component, the changeover component being arranged to then engage the second feature so as to rotate the second support to a position from which the indexing mechanism is arranged to rotate the second support.

In this way, a single indexing mechanism may be provided to rotate the first and second supports in sequence with changeover being achieved automatically by means of the changeover component.

Preferably, the changeover component rotates to the second support from a position at which the indexing mechanism does not rotate the second support and, when the first support moves the changeover component, the first support moves to a position which the indexing mechanism does not rotate the first support.

When the second support is rotated back around to the position at which the indexing mechanism does not rotate the second support, consecutive operations of the indexing mechanism preferably cause no rotation of either support.

In this way, the device is automatically prevented from indexing carriers to pockets which have already been used.

The changeover mechanism allows the same indexing mechanism to initially index a first carrier disc and then, at a predetermined location, index both carrier discs together for one increment and then subsequently cause the indexing mechanism to only index the second carrier disc.

The changeover action can be initiated solely by the angular position of the first carrier disc requiring no other input from the user and providing insignificant difference in the tactile feedback.

Preferably, the changeover component is supported freely between and by the first and second components.

Preferably, the device further includes a dose counter having a first counter ring having an indication of unit counts on a first display surface, the first counter ring being rotatable about a counter axis, a second counter ring having an indication of tens counts on a second display surface, the second counter ring being rotatable about the counter axis and a Geneva mechanism for driving the second counter ring from the first counter ring and rotating the second counter ring between consecutive tens counts when the first counter ring rotates between two predetermined unit counts.

In this way, the user is provided with an indication of the doses used or the doses remaining.

By providing two counter rings respectively for units and tens, relatively large display figures may be provided, while still allowing a large number of counts, for instance 40, 60 or 80. The Geneva mechanism provides a particularly effective way of allowing the tens counter ring to be incremented as required.

Preferably, the first counter ring is driven with rotation of the first support.

Hence, the count of unit doses dispensed is incremented/decremented automatically with each indexing of the device. The first counter ring may include gear teeth around its outer periphery and an intermediate gear may be provided to drive it from the indexing mechanism. Where, as described above, the indexing mechanism includes a Geneva wheel, the intermediate gear can be driven directly from the Geneva wheel.

Preferably, the counter axis is coaxial with the first support.

Hence, the first and second counter rings may rotate about the same axis as the carriers and their supports. This allows a particularly compact arrangement.

According to the present invention, there may also be provided a device for dispensing individual doses of powder from respective pockets of a carrier, the device including an indexing mechanism for indexing the carrier between respective pockets, a first counter ring having an indication of unit counts on a first display surface, the first counter ring being rotatable about a counter axis, a second counter ring having an indication of tens counts on a second display surface, the second counter ring being rotatable about the counter axis and an intermittent-motion mechanism for driving the second counter ring from the first counter ring and 5. rotating the second counter ring between consecutive tens counts where the first counter ring rotates between two predetermined consecutive unit counts, the first counter ring being driven with the indexing mechanism.

Preferably, the intermittent-motion mechanism is a Geneva mechanism.

Hence, as described above, this allows a large number of counts to be provided with relatively large display numerals.

Preferably, the first and second counter rings are positioned one within the other, with the first and second display surfaces adjacent each other.

The display surfaces may thus be generally planar (and perpendicular to the counter axis).

Preferably, the second counter ring may be positioned within the first counter ring, the first counter ring may include a pin for engaging a Geneva wheel rotatable about an axis offset from the counter axis and the second counter ring may include features engageable by the Geneva wheel.

In this way, during a complete revolution of the first counter ring, at a predetermined position of that revolution, a pin may engage the Geneva wheel so as to rotate it and, hence, rotate the second counter wheel by one increment. This arrangement allows a particularly compact design.

According to the present invention, there is also provided a device for dispensing individual doses of powder from respective pockets of a carrier, the device including: an indexing mechanism for indexing the carrier between respective pockets; a first counter ring having an indication of unit counts on a first display surface, the first counter ring being rotatable about a counter axis; a second counter ring having an indication of tens counts on a second display surface, the second counter ring being rotatable about the counter axis; and a mechanism for rotating the second counter ring between consecutive tens counts when the first counter ring rotates between two predetermined consecutive unit counts, the first counter ring being driven with the indexing mechanism; wherein the first and second counter rings are positioned one with the other, with the first and second display surfaces adjacent each other.

It will be appreciated that devices according to the present invention can be provided with or without carriers.

BRIEF DESCRIPTION OF THE DRAWINGS

The invention will be more clearly understood from the following description, given by way of example only, with reference to the accompanying drawings in which:

FIG. 10 illustrates the chassis and cam member assembly of the preferred embodiment;

FIG. 13 illustrates sub-assemblies of the preferred embodiment;

FIGS. 19(a) to (d) illustrate the Geneva mechanism of a counter in an embodiment of the present invention;

DETAILED DESCRIPTION OF THE DRAWINGS

Figure 1A:
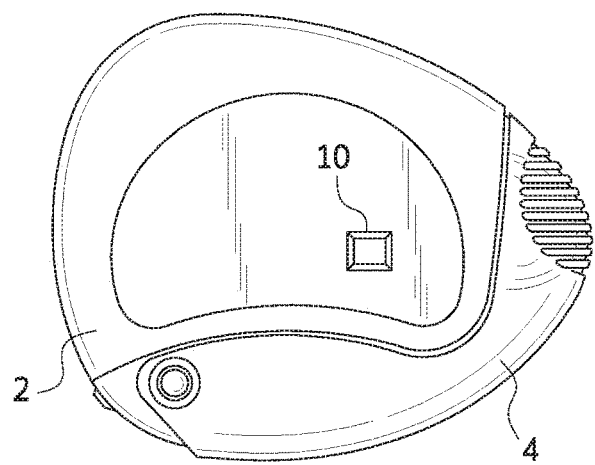
FIGS. 1(a) to (c) illustrate operation of an assembled device according to the present invention.

A preferred embodiment of the present invention is an inhalation device from which a user may inhale consecutive doses of medicament in the form of dry powder. The preferred embodiment is illustrated in FIGS. 1(a) to (c).

The device includes a housing 2 on which a mouthpiece cover 4 is rotatably supported.

In order to use the device, the mouthpiece cover 4 is rotated away from the housing 2. As illustrated in FIG. 1(b) this exposes a mouthpiece 6. The mouthpiece 6 may be formed integrally with the housing 2, but, as will be described below, it can also be formed as a separate component for mounting with the housing 2. This allows the material properties, for instance, colour, of the mouthpiece 6 and housing 2 to be varied easily according to the requirements of the device.

Figure 1B:
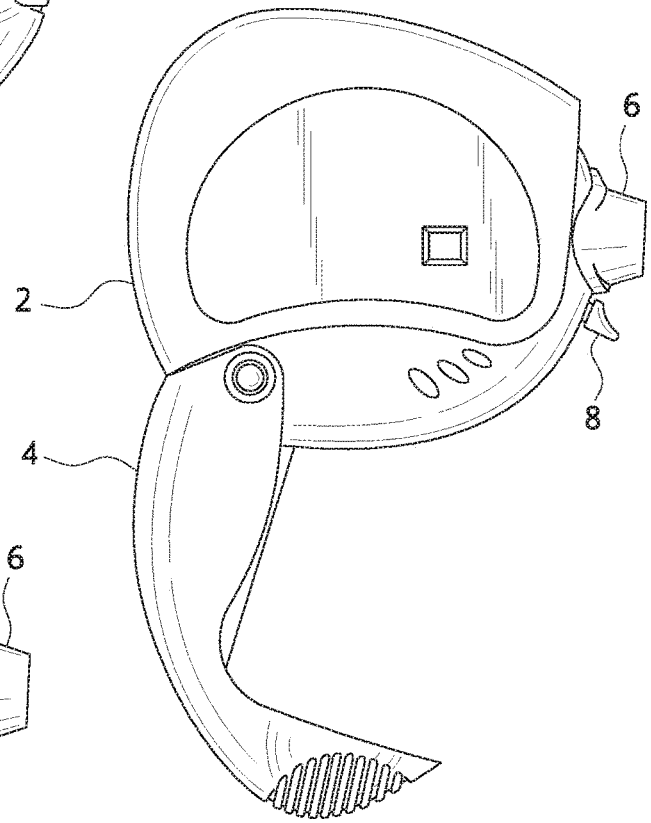
Figure 1C:
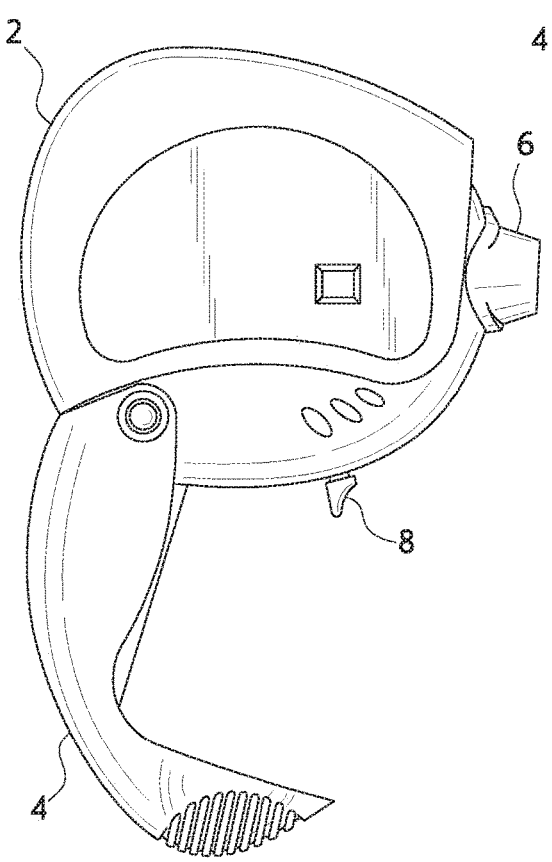

As illustrated in FIG. 1(b), a priming lever 8 extends out of the housing 2 at a position adjacent the mouthpiece 6. The priming lever 8 is mounted so as to rotate about a central axis within the device (to be discussed further below). In this way, it is moveable by the user around a periphery of the housing 2 to a position as illustrated in FIG. 1(c). Movement of the priming lever 8 from the first position illustrated in FIG. 1(b) to the second position illustrated in FIG. 1(c) is arranged to prime the device, in particular, to expose a dose of powder such that it may be carried with an airstream out of the mouthpiece 6.

It should be noted that locating the first position of the priming lever 8 adjacent the mouthpiece 6 is highly advantageous, since it discourages a user from attempting to inhale from the mouthpiece 6 before moving the priming lever 8 away from the mouthpiece 6 to the second position of FIG. 1(c). In other words, the user is encouraged to prime the device before attempting to inhale through it. Nevertheless, it should be noted that a small space is preferably provided between the mouthpiece 6 and priming lever 8 so as to allow the user to operate the priming lever 8 with his or her finger without touching the mouthpiece 6.

After use of the device, the mouthpiece cover 4 may be rotated back to its stowed position illustrated in FIG. 1(a). In this respect, an inner surface of the mouthpiece cover 4 is provided with a return actuator for engaging with the priming lever 8. In particular, when the mouthpiece cover 4 is moved from its open position of FIGS. 1(b) and (c) to its closed position of FIG. 1(a), the return actuator engages with the priming lever 8 and moves it back from its second position illustrated in FIG. 1(c) to its first position illustrated in FIG. 1(b). As will be described further below, in the preferred embodiment, this movement of the priming lever 8 operates an indexing mechanism for moving a still unused and unopened pocket of powder into line with a dispensing mechanism such that, with subsequent priming of the device, the powder of that pocket is dispensed for inhalation. By operating the indexing mechanism during the return movement of the priming lever 8 immediately after priming and release of a pocket of powder, if the released powder is not inhaled, it is indexed to a position where it can safely be held within the device.

As illustrated in FIGS. 1(a) to (c), the preferred embodiment also includes a window 10 in one side of the housing 2. The window 10 is provided so as to allow a user to view a counter display within the device. A counter mechanism indexes the counter display upon each use of the device so as to provide the user with an indication of how may doses have been dispensed and/or how may doses remain unused.

Many aspects of the present invention are applicable to devices housing a wide variety of different dose carriers. In particular, many of the features of the embodiment described below can be used with carriers having a traditional blister-pack construction, with carriers having various arrays of pockets and, in some arrangements, with some carriers having a single respective pocket. Nevertheless, the present invention is particularly advantageous when used with carriers of the form illustrated in FIGS. 2(a) and (b).

Figure 2A:
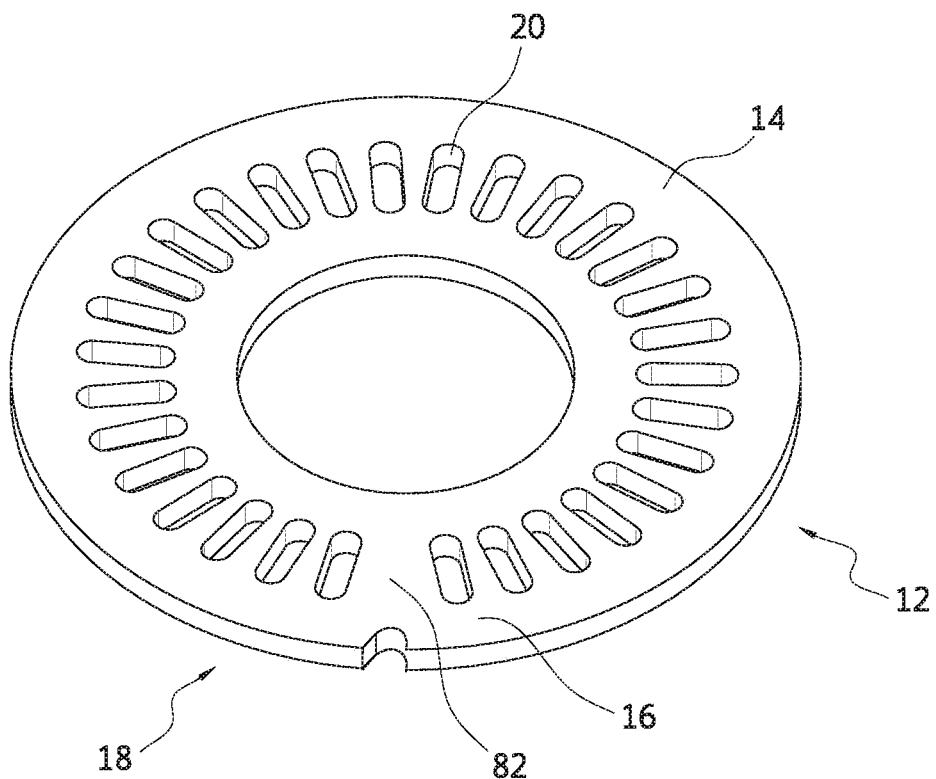
FIGS. 2(a) and 2(b) illustrate a carrier for use with the present invention without and with its lidding sheets.

As illustrated in FIG. 2(a), each carrier 12 is formed from a disc-shaped base 14 having a substantially planar first side surface 16 opposite and parallel with a substantially planar second side surface 18. A plurality of through holes 20 are formed between the first and second side surfaces 16, 18 so as to form spaces for housing doses of powder. The base 14 is formed with an appreciable thickness so as to provide the through holes 20 with sufficient space to house the required doses of powder. The through holes 20 are arranged as a circumferential array and, in the preferred embodiment, 30 through holes are provided in the array.

Figure 2B:
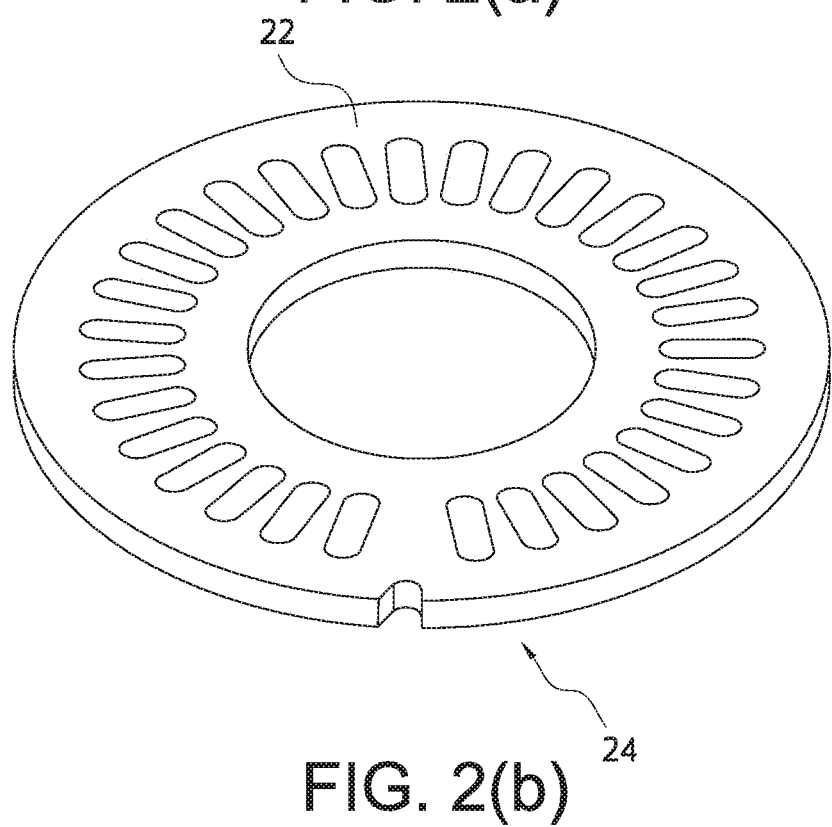

As illustrated in FIG. 2(b), the first and second side surfaces 16, 18 of the base 14 are sealed with respective first and second lidding sheets 22, 24. In this way, the carrier 12 provides a plurality of pockets housing individual respective doses of powder.

Figure 3A:
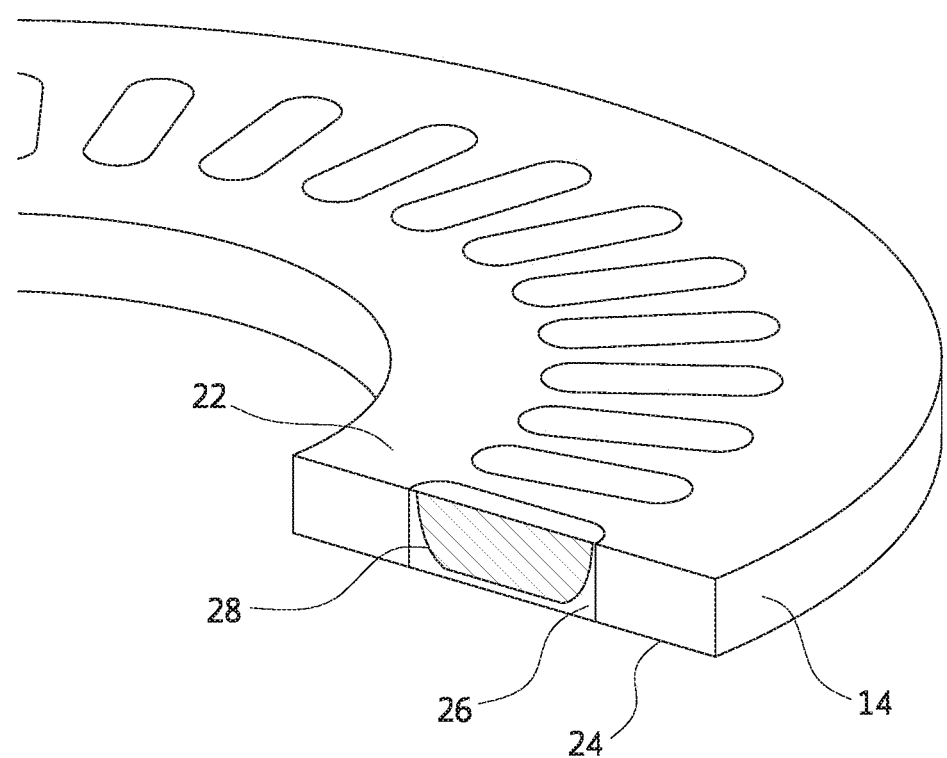
FIGS. 3(a) and (b) illustrate movement of an insert from the carrier of FIGS. 2(a) to (c)
Figure 3B:
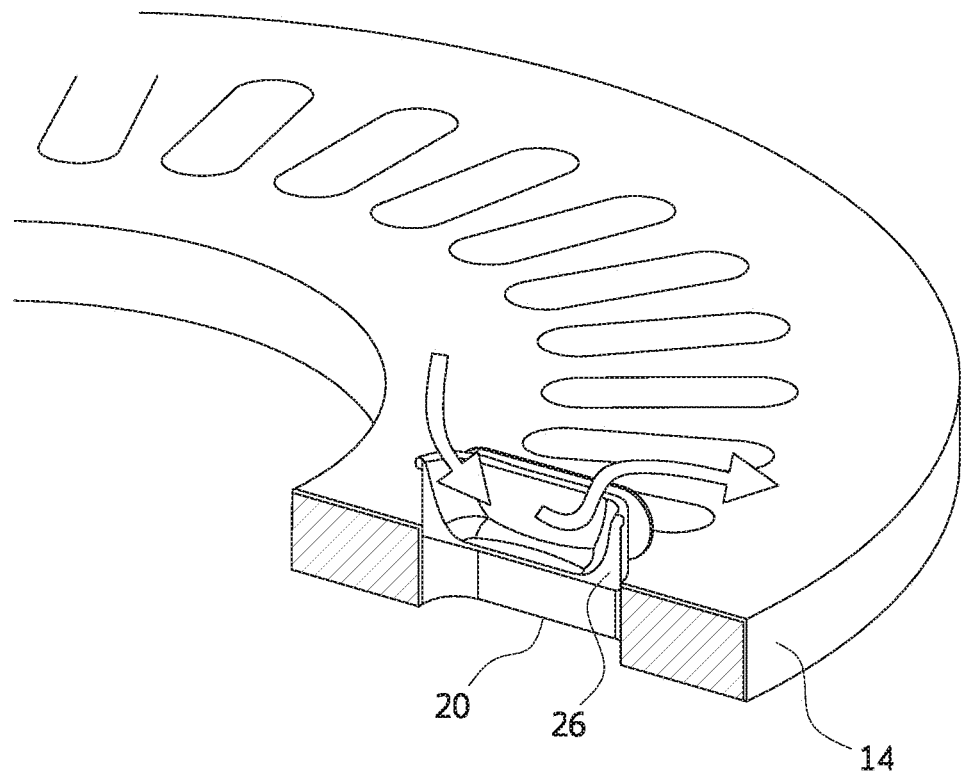

As illustrated by the cross-sections of FIGS. 3(*a*) and (*b*), the pockets preferably include a respective insert 26 within each through hole 20. The inserts 26 are generally cup-shaped with their open ends facing the first lidding sheet 22. Each contain a respective dose of powder 28.

By pushing on the closed end of the insert 26 from the side of the second lidding sheet 24, it is possible to push the insert 26 outwardly from the base 14 of the carrier 12 through the first lidding sheet 22. This is illustrated in FIG. 3(*b*), but, for clarity, without either lidding sheet. As illustrated, with the insert 26 extending out of the base 14, it may be more convenient to provide an airflow (such as indicated by arrows) to remove powder from the pocket.

Figure 4A:
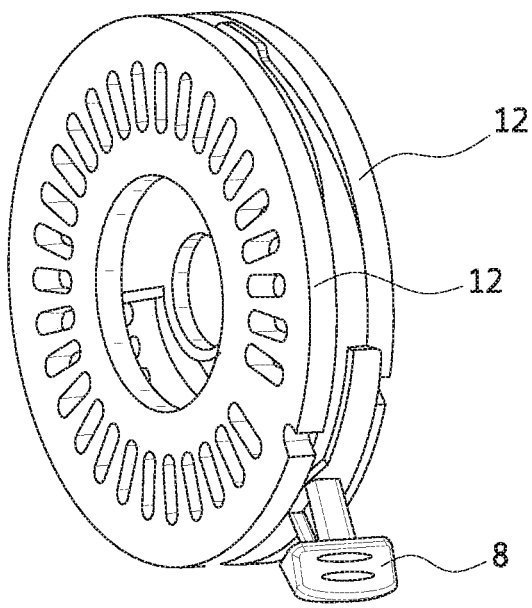
FIGS. 4(a) and (b) illustrate a preferred arrangement for carriers within the device without and with supports of the device.
Figure 4B:
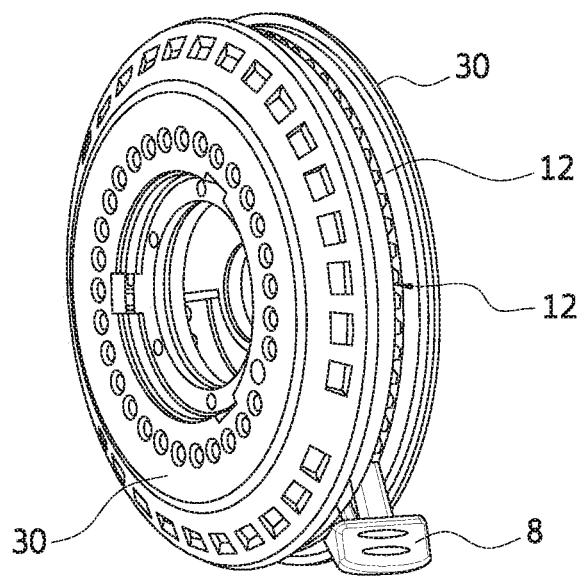

Within the housing 2 of the inhalation device, in a preferred embodiment, two of the carriers 12 are arranged coaxially side by side as illustrated in FIG. 4(*a*). Each carrier 12 is provided with a support 30 as illustrated in FIG. 4(*b*). In the illustrated embodiment, each support 30 is positioned adjacent an outwardly facing surface of its respective carrier 12. In particular, the first side surface 16 of each carrier 12 faces a respective support 30 such that a dispensing mechanism may be provided between the two carriers 12 so as to press respective inserts 26 outwardly towards the respective supports 30. The preferred arrangement for this will be described further below.

As illustrated, the priming lever 8 is positioned such that it extends between the carriers 12 and is rotatable about the common axis of the carriers 12 so as to operate a dispensing mechanism and an indexing mechanism.

Figure 5A:
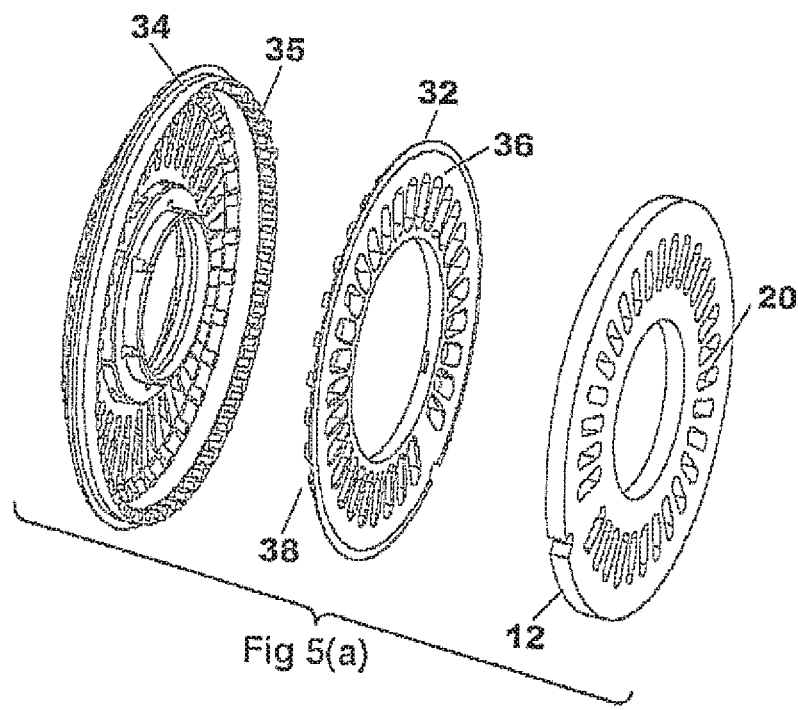
FIGS. 5(a) and (b) illustrate airway plates and anvil plates of the device in conjunction with corresponding carriers.
Figure 5B:
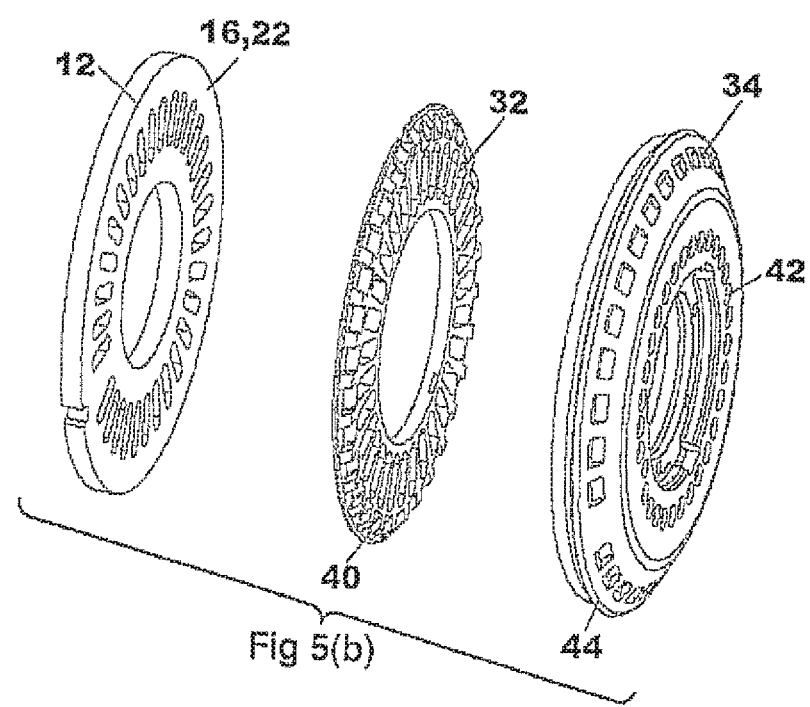

In the preferred embodiment, each support 30 is made up of two components, namely an anvil plate 32 and an airway plate 34. These are illustrated in FIGS. 5(*a*) and (*b*) in conjunction with associated carriers 12.

Each anvil plate 32 has a planar surface 6 which-, in use, abuts against the first side surface 16 of the associated carrier 12 as covered by the first lidding sheet 22. Each anvil plate 32 also includes a plurality of guide through holes 38 corresponding to the through holes 20 of the associated carrier 12.

Figure 6:
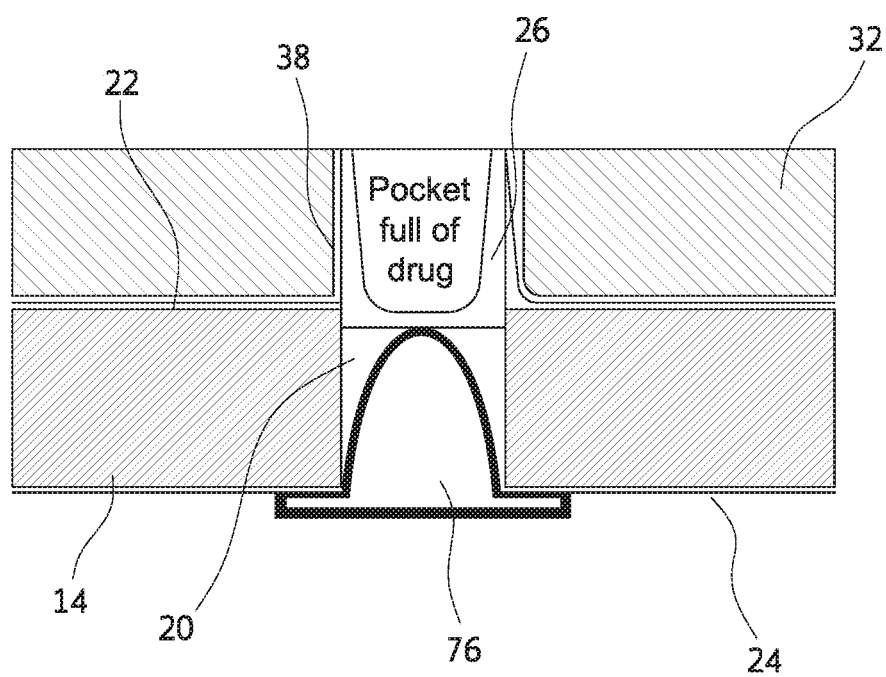
FIG. 6 illustrates an insert of a carrier pushed into its corresponding anvil plate.

In this way, as illustrated schematically in FIG. 6, an insert 26 can be pushed out of its through hole 20 and into a corresponding guide through hole 38 of the anvil plate 32. The insert 26 is thus used to outwardly burst through the first lidding sheet 22, but is still held securely in place. Although not of a particular concern here, the anvil plate 32 also supports the first lidding sheet 22 around the through hole 20 and can be used to improve the predictability of the nature of the lidding sheet rupture.

Figure 7A:
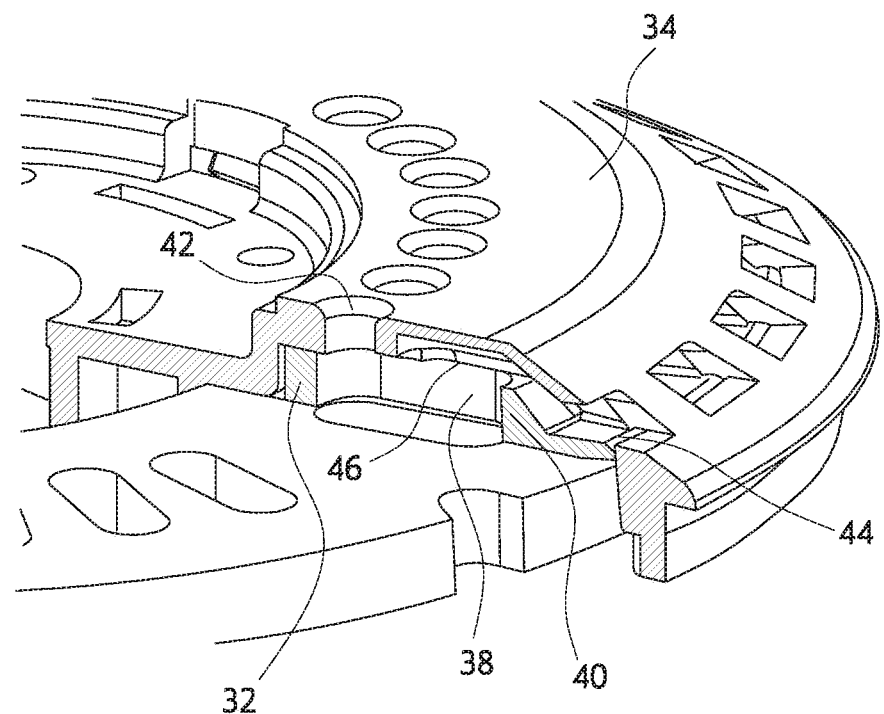
FIGS. 7(a) and (b) illustrate movement of an insert of a carrier plate into a corresponding anvil plate.
Figure 7B:
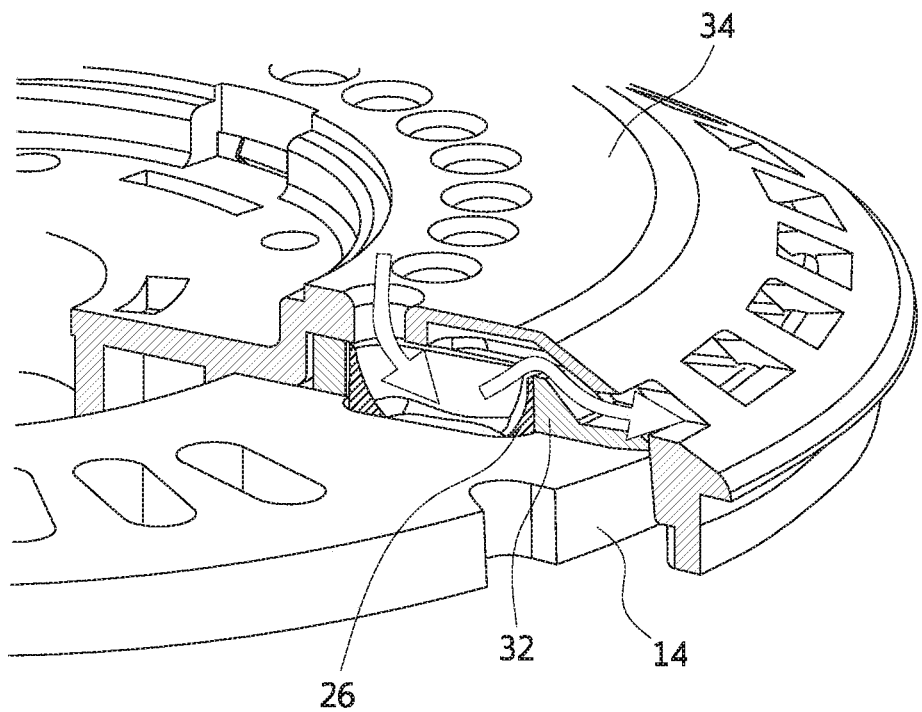

As illustrated by the cross-section of FIG. 7(*a*), the anvil plate 32 includes a second surface 40 which abuts an inner surface of the associated airway plate 34. The airway plate 34 includes a pair of through holes corresponding to each guide through hole 38 of the corresponding anvil plate 32. In particular, each pair includes an inlet hole 42 and an outlet hole 44.

As illustrated in FIG. 7(*a*), relative to the surface 40 of the anvil plate 32 abutting the inner surface of the airway plate 34, a recessed channel 46 extends radially inwardly from the outlet 44 so as to communicate with the guide through-hole 38 of the anvil plate 32. Hence, for each guide through hole 38 of the anvil plate 32, the airway plate 34 provides, communicating with it, a corresponding inlet 42 and outlet 44 with its associated recessed channel 46. In particular, each inlet 42 communicates with one side of its associated guide through hole 38 whilst the corresponding outlet 44 communicates with the opposite side of the associated guide through hole 38.

As illustrated in FIG. 7(*b*), when an insert 26 is pushed outwardly of the through hole 20 of the base 14 into the guide through hole 38 of the anvil plate 32, it is positioned with the open portion of its cup-shape facing the inlet 42 (at one end of the cup-shape) and the recessed channel 46 (at the opposite end of the cup-shape). In this way, as illustrated, an airflow may be drawn through the airway plate 34 such that it passes down into the pocket formed in the insert 26, back up into the recessed channel 46 and then out of the outlet 44. Powder in the insert 26 is thus picked up by the airstream, removed from the insert 26 and carried out of the airway plate 34. A flow path is thus formed into and out of a pocket which may then connect the pocket to the mouthpiece 6 of the device.

Figure 8:
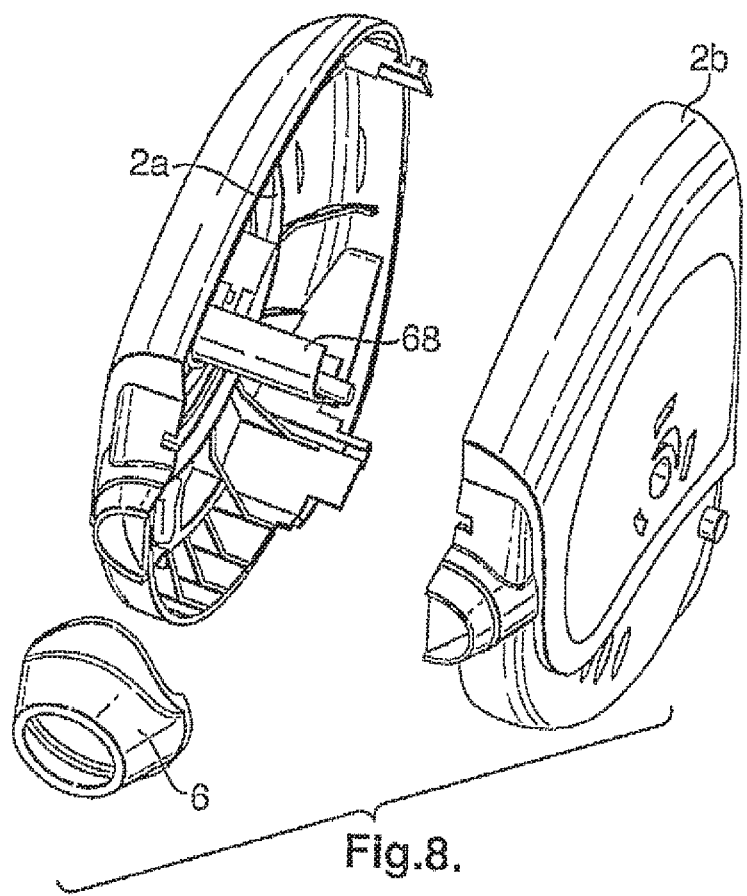
FIG. 8 illustrates the housing of the preferred embodiment.

As illustrated in FIG. 8, the housing 2 may be formed from a pair of casing halves 2*a* and 2*b*. As illustrated in FIGS. 9(*a*) and (*b*), an inner wall 50 of the casing halves 2*a* and 2*b* cooperates with the airway plate 34 so as to form a second flow path to the mouthpiece 6 which bypasses the pocket(s). Alternatively, an additional component may be provided, to define the second flow path.

As illustrated in FIG. 9(*b*), for each pocket formed by an insert 26, the corresponding inlet 42 of the airway plate 34 is positioned adjacent a periphery of the pocket. The corresponding outlet 44 is provided on an opposite side of the pocket such that the airstream between the inlet 42 and outlet 44 crosses the pocket and, hence, picks up any powder from the pocket.

As illustrated, the inlet 42 is formed as a portion which is directed down into the insert 26 forming the pocket.

In this way, when a user inhales through the device and creates an airstream through it, the airstream drawn through the inlet 42 will be directed down into any powder in the insert 26 so as to dislodge it and move it into the airstream so as to be carried out of the outlet 44. In the illustrated embodiment, the recessed channel 46, which connects the volume of the pocket to the outlet 44, is positioned adjacent the inlet 42. In this way, the airstream from the inlet 42 is deflected from the base of the insert 26 (and any powder there) so as to travel back towards the recessed channel 46. Powder carried in the airstream up into the recessed channel 46 is subjected to a relatively sharp change in direction. As a result of this, powder in the airstream tends to be deaggregated. Furthermore, the powder will tend to hit the surfaces of the recessed channel 46 also contributing to deaggregation.

As is clear from FIG. 9(*b*), the shape of the airway path is chosen to force large aggregates of powder to impact the walls as the airflow is forced to change direction, thereby deaggregating large clumps of powder. The shape is also designed to ensure that airflow over any surface within the airway is maintained at a high value to avoid excessive powder adhering to the surface. Thus corners are rounded and the cross section at each position along the tube is designed to maintain air velocity without generating excessive pressure drop.

As illustrated in FIG. 9(*a*), in this embodiment, the airflow through the pocket has its minimum area at the inlet to the pocket defined by the dimension "a" whereas the airflow that bypasses the pocket has its minimum cross section just before the airflow join and so is defined by the dimension A.

The air velocity is highest where the cross sectional area is smallest so this arrangement provides high velocity air to extract the powder from the pocket and uses the high velocity of the bypass air joining the powder contained in the pocket airflow to assist de-aggregation and to protect the walls from powder deposition.

The airflow velocity through the pocket is controlled mainly by the suction pressure created as the user inhales, whereas the volume flow rate is a factor of both velocity and area.

A sufficiently high air velocity should be generated to ensure that the powder is entrained in the airflow. However, if the velocity—and flow volume are too high then there is the possibility that the whole of the mass of powder in the pocket is pushed through the airway as an agglomerated clump. If this happens, the clump may not accelerate to a sufficient velocity for its impact with the walls in the airway to break it up and provide de-aggregation. It is preferred that the powder is removed gradually from the pocket by the airflow. To achieve this, a small gap 46a is provided between the surface of the powder in the pocket and the airway roof formed from the division in the airway plate 34 between the inlet 42 and recessed channel 46. This, combined with a dimension for "a" that limits the flow volume through the pocket, ensures that the powder is eroded from the pocket rather than pushed out.

To enable this, the inlet hole diameter "a" is chosen to be between 0.5 mm and 2.0 mm for pockets—of around 2.0 mm width (in a circumferential direction) and of around 7.3 mm length (in a radial direction). The value chosen depends on the properties of the powder.

In this way, the powder can be removed from the pocket over a time period ranging from between 0.1 s to 1.0 s. This is within the period of the high flow rate of the inhalation cycle and provides good de-aggregation of the powder.

It should be appreciated that, in other embodiments, it is possible for parts of the flow path through the pocket, other than the inlet hole, for instance downstream of the powder, to form the minimum cross-sectional area of that flow path. Similar considerations will still apply for the diameter "a" of the inlet hole.

The arrangement of the inlet hole 42 and channel 46 is particularly advantageous in conjunction with deep narrow pockets of powder. At a particular flow rate, for instance 10 ltr/min, the surface of the powder will be eroded by a certain depth. Increasing the flow rate to, for instance 20 ltr/min, will result in the powder being eroded by a further depth. Since inhalation by users results in flow rates which increase progressively to a maximum, powder is eroded depth by depth and the pocket is emptied gradually over an appropriate period.

Although the volume and strength of inhalation will vary between users, it is important that the device should not provide too much in the way of resistance to inhalation. In this respect, it would be extremely difficult to inhale through an inlet 42 having a desired cross sectional area. Indeed, where possible, it would result in a flow velocity which was far too high and which would entrain of all of the powder from the insert 26 far too quickly. In practice, it is found that approximately only 20% of inhaled air can be used directly for picking up and deaggregating the powder.

Figure 9A:
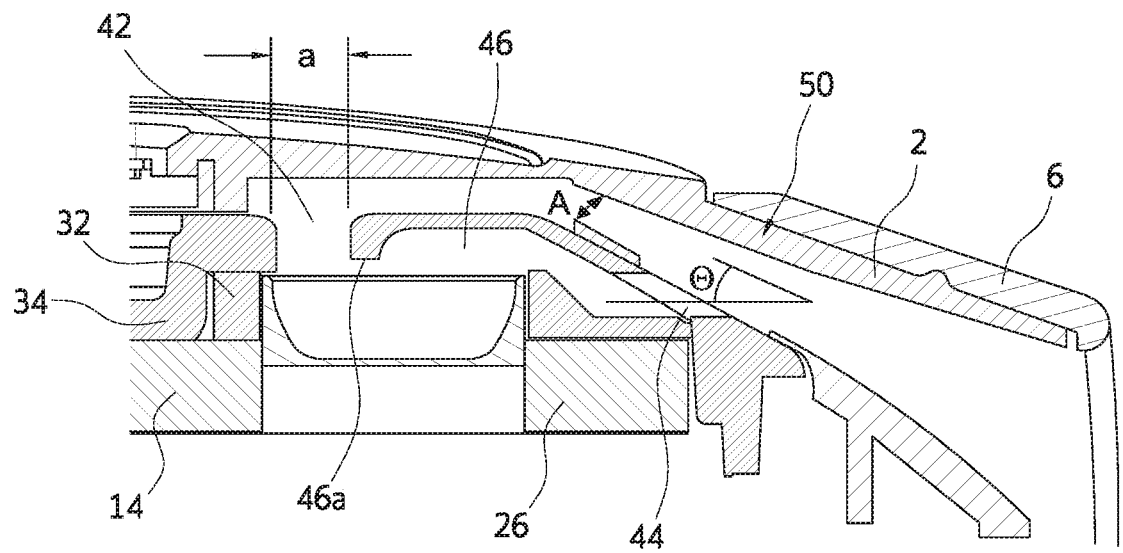
FIGS. 9(a) and 9(b) illustrate airflow paths through the preferred embodiment.
Figure 9B:
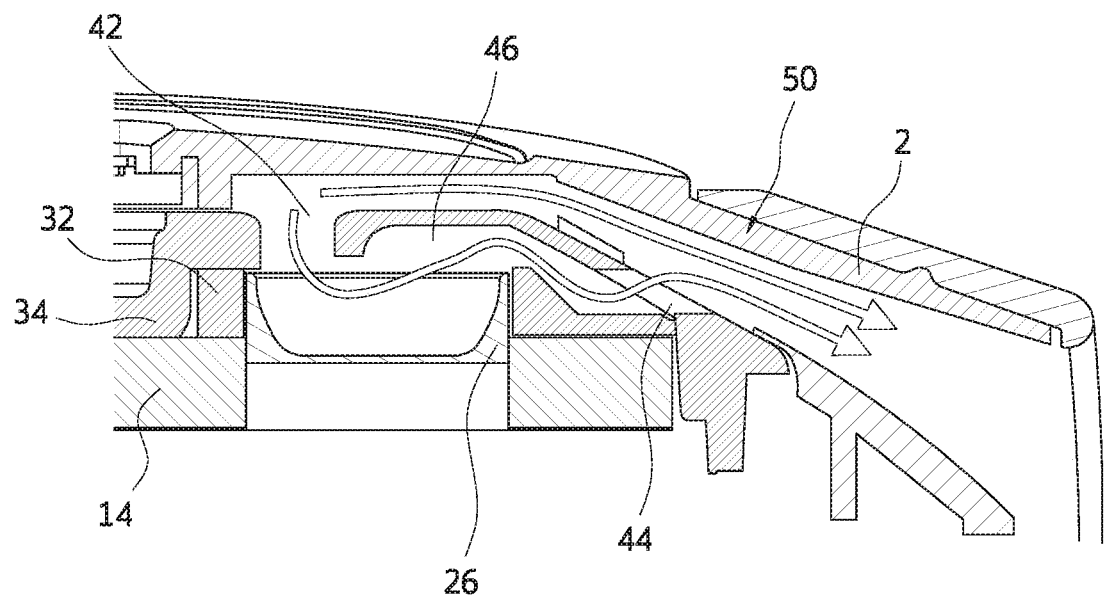

As illustrated in FIG. 9(b), a second flow path is formed between an inner wall 50 of the housing 2 and the outside of the airway plate 34. The second flow path bypasses the pocket and increases the overall cross sectional area available through which to inhale. By changing the values of the dimensions a and A, it is possible to change the rates of airflow between the pocket and bypass and to control the overall flow resistance of the device so that it is comfortable for the user to inhale through. A typical flow resistance for the device would be between 2 kPa and 5 Kpa for a flow volume of 60 l/min. Higher flow resistances are chosen for powders which are harder to deaggregate, whereas lower flow resistances are preferred for devices used by children. The recessed channel 46 and outlet 44 generally have larger cross sectional areas than the inlet 42. It is envisaged that the minimum cross sectional area for the pocket path would be 3.5 mm$^2$ to 4.0 mm$^2$ and for the bypass 5.0 mm$^2$ to 6.0 mm$^2$.

In this way, it is relatively easy to inhale through the device, since a large proportion of the airflow will be through the second flow path. Nevertheless, some of the flow will occur through the first flow path so as to entrain and deaggregate the powder as described above.

In the preferred embodiment, there is another second flow path for the other side of the device and its corresponding carrier. In use, a patient inhales through both second flow paths whilst drawing powder from the first flow path in use. Each of the second flow paths is expected to carry approximately 40% of the total inhaled air for an average use.

Actual requirements will vary depending upon the nature of the powder and the intended user. For an easily dispensed powder, the portion forming the inlet to the pocket can be small and, for a child or patient with COPD (Chronic Obstructive Pulmonary Disease), the total pressure drop should be low. In this case, an inlet portion could be provided with a cross-sectional area of 2 mm$^2$ and a bypass second flow path with a minimum cross-sectional area of 8 mm$^2$, resulting in a ratio of 25%). On the other hand, with sticky powder for a healthy adult, the inlet portion could be provided with a cross-sectional area of 4 mm$^2$ together with a bypass second flow path having a minimum cross-sectional area of 6 mm$^2$, resulting in a ratio of 66%. Of course, intermediate values are also possible and a preferred arrangement has an inlet portion of approximately 3 mm$^2$ with a second flow path minimum cross-sectional area of 6 mm$^2$, resulting in a ratio of 50%.

As illustrated in FIG. 9(a), the walls of the outlet 44 are orientated so as to direct the flow of air and powder into the second flow path at an angle θ relative to the flow in the second flow path. By ensuring that the angle θ is less than 45°, it is possible to substantially reduce the amount of powder which might impact with or stick to the wall 50 opposite the outlet 44. Preferably the angle θ is no greater than 45°, more preferably no greater than 30°. In this way, substantially no powder will adhere to the wall 50 forming the second flow path to the mouthpiece 6. Preferably, with repeated use of the device, no more than 25%, preferably no more than 15% of a dose remains deposited on the wall 50. In this respect, it will be appreciated that the flow from the bypass past wall 50 will act to scour or scavenge powder from the wall 50.

As mentioned above with reference to FIG. 4(b), the anvil plate 32 and airway plate 34 together form a support for a corresponding carrier 12. By means of the priming lever 8 and the indexing mechanism to be described below, a support 30 and its corresponding carrier 12 is moved to consecutive-positions to dispense powder from consecutive pockets. In this regard, it will be appreciated that each pocket has its own first flow path as formed in the airway plate 34. From the description above, it will be appreciated that turbulent flow in removing powder from the pocket and deaggregation of powder occurs within the first flow path. Thus, should any powder adhere to walls within the airway plate 34, this powder is not available for inhalation when subsequent pockets of powder are dispensed.

The device is preferably arranged such that an inlet passage that provides the air for the flow through the pocket and through the bypass is arranged so that it feeds the air only to the pocket positioned for dispensing, such as illustrated in FIGS. 9(a) and (b). The indexing of the carrier 12, anvil plate 32 and airway plate 34 after use repositions the inlet 42 and outlet 44 for a used pocket outside of the airflow for the pocket currently in use.

This arrangement ensures that, even if none of the powder from a pocket is removed after it has been opened, once it has been indexed on, then the powder will be permanently retained within the device such that it will not be inhaled along with a subsequent dose.

The supports 30 and associated carriers 12 may be rotatably mounted within the housing 2 by means of a chassis sub-assembly 58 as illustrated in FIG. 10. The chassis sub-assembly 58 is positioned between the second side surfaces 18 of the carriers 12. It extends axially along the axis of the carriers 12 and is fixed to one or both of the two halves 2a, 2b of the housing 2.

As illustrated in FIG. 10, the priming lever 8 forms part of (or could be attached to) a priming member 60. The priming member 60 has a central pivot opening 62 by which it is rotatably supported on a pivot shaft 64 of a chassis 66.

As illustrated in FIG. 13, the priming member 60 and chassis 66 are together positioned between the two carriers 12 and associated supports 30. Furthermore, the chassis 66 is mounted to the housing 2 so as to be rotatably fixed. In the illustrated embodiment, the pivot shaft 64 may itself be located on a shaft 68 provided on the inside of one or both halves 2a, 2b of the housing 2. Also, a radial extension 70 (shown in FIG. 10) may be provided on the chassis 66 to interact with an inner portion of the housing 2 so as to rotationally fix the chassis 66.

The carriers 12 and associated supports 30 may be rotationally mounted on the chassis 66.

The priming member 60 includes an elongate cam member 72 which extends in a circumferential direction and has a cam surface 74 on each of two opposites sides.

Each cam surface 74 interacts with a respective member 76 which will be described as a prodger.

Operation of the priming member 60, cam member 72, cam surfaces 74 and prodgers 76 will be described with reference to the schematic illustration of FIG. 11.

Figure 11:
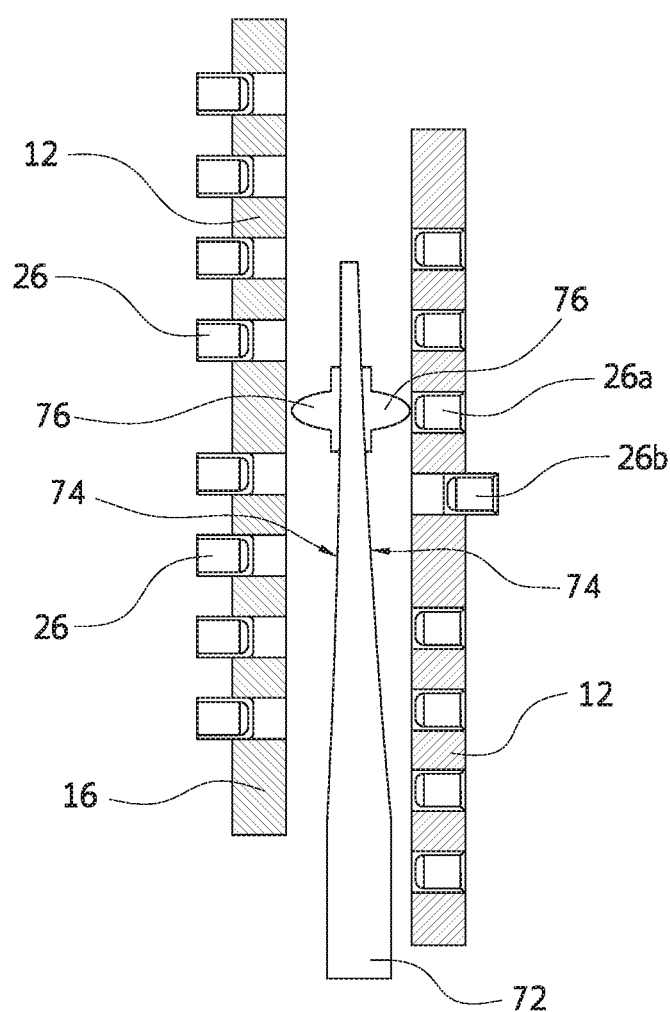
FIG. 11 illustrates schematically operation of the dispensing mechanism of the preferred embodiment.

When the priming lever 8 is moved from its first position to its second position, the priming member 60 is rotated relative to the chassis 66, the carriers 12 and their supports 30 such that, in the schematic illustration FIG. 11, the cam member 72 moves upwardly.

As can be seen in FIG. 10, the priming member 60 includes elongate openings either side of the cam member 72 through which arms 80 of the prodgers 76 can extend. The chassis 66 holds the prodger 76 rotationally but allows them to move in an axial direction of the device, in other words towards and away from the carriers 12 on either side. Indeed, as illustrated, an aperture 82 exists in the chassis 66 allowing one of the prodgers 76 to extend through the chassis 66 towards a corresponding carrier 12.

As illustrated in FIG. 11, the cam surface 74 on either side of the cam member 72 is such that, as the priming member 60 rotates and the cam member 72 moves upwardly as illustrated in FIG. 11, the prodgers 76 are moved outwardly towards their respective carriers 12.

In FIG. 11, the right hand prodger 76 is illustrated in alignment with a pocket in its corresponding carrier 12. Thus, when the priming member 60 rotates and the cam member 72 moves upwardly in FIG. 11, the right hand prodger 76 will be moved outwardly towards its corresponding carrier 12, will penetrate the through hole 20 and push the insert 26a out of the first side surface 16. In this respect, FIG. 11 illustrates one insert 26b which has already been pushed out by the prodger 76.

An indexing mechanism, to be described below, rotates the right hand carrier 12 and its corresponding support 30 to the next position in which the prodger 76 is aligned with a new, unopened pocket. The operation of opening a pocket can then be repeated.

It will be appreciated from FIG. 11 that carriers 12 on either side of the priming member 60 could have respective pockets aligned with the prodgers 76 such that operation of the cam member 72 simultaneously opens pockets of the respective carriers 12. However, in the illustrated embodiment, the indexing mechanism arranges for one of the prodgers 76 to be aligned with a pocket whilst the other of the prodgers 76 is at a position between pockets. In this way, the dispensing mechanism formed from the cam member 72 and prodgers 76 only opens one pocket at a time.

Referring to FIG. 2(a), it will be seen that the preferred carrier 12 has an array of through holes 20 which includes a space 82 in which a through hole 20 is not formed.

Using carriers of this type, it is possible to position one carrier 12 with the blank portion 82 opposite a prodger 76 whilst consecutively indexing the other carrier 12 around each of its through holes 20 and the pockets they form until all have been emptied. The indexing mechanism can then rotate the empty carrier to a position in which its blank portion 82 is opposite the prodger 76 and rotate the other carrier 12 around all of the positions in which the corresponding prodger 76 aligns with the through holes 20. In this way, the same dispensing mechanism is used for dispensing powder from both carriers and using the same operation.

Although it is the intention that substantially all of the powder dispensed from the individual pockets will be removed from the device by way of inhalation, it is possible that some powder will remain within the device. Indeed, where different types of carrier are used or the device has a different application, it might be that more powder does remain within the device.

As illustrated in FIG. 10, the cam surfaces 74 are provided with one or more grooves or channels 84. Any excess powder can thus fall into the grooves 84 such that contact and movement between the cam surface 74 and the prodger 76 is not impeded.

It will be appreciated that, with the arrangement where one or other of the prodgers 76 abuts a portion 82 of a carrier 12 where there is no pocket, in order for the priming member 60 to rotate and the cam member 72 to move a prodger 76 towards the other carrier 12, it will be necessary for the cam member 72 to move away from the portion 82. In some embodiments, it might be possible to allow the entire priming member 60 to move axially or for the carriers 12 to move axially. However, in the preferred embodiment, the cam member 72 has itself a limited amount of flexibility. As illustrated, the cam member 72 is provided as an elongate member which is attached to the rest of the priming member 60 at each end with an elongate opening either side of it. This will allow sufficient flexibility for the cam member 72 to move towards and away from the carriers 12.

Considering the overall embodiment as described with reference to FIG. 1(*a*) to (*c*), it will be appreciated that it is highly desirable to ensure that the user moves the priming lever 8 through its entire length of travel so as to fully dispense a dose of powder. In particular, considering FIG. 11, it would be undesirable for a user to partly operate the priming lever 8 and priming member 60 such that a prodger 76 pushes an insert 26 far enough to partly rupture a lidding sheet on the first side surface 16, but without fully extending the insert 26 to the position illustrated in FIGS. 6 and 7(*b*).

As the motion of the inserts 26 is restricted by the foils 22, 24 sealing both surfaces of the carrier plate 12, a high force is required to cause the inserts 26 to start to move. This force increases to the point at which the foils 22, 24 rupture after which the force decreases substantially. Thus, the user feels a resistance to the motion of the priming lever 8 for the early part of its travel. At some point along its travel, the resistance suddenly reduces, as the foil 22, 24 rupture. The user cannot reduce the applied force instantaneously so that the priming lever 8 is rapidly pushed to the end of its available stroke. This tactile feedback encourages the user to fully open the pockets.

If the cam member 72 driving the prodgers 76 was solid as shown in FIG. 11, then the inserts 26 would be forced to the positions shown. However, in the preferred embodiment where the parts are moulded in plastic, it is impossible to control the dimensions of all parts with absolute accuracy. Thus, where the distance moved by the insert 26 is smaller than the space allowed for it, there would be a gap above the pocket but where the distance moved is greater than the distance allowed for it, the anvil plates 32 would be pushed apart from the carriers 12 by the force. This force would be transmitted to the casework causing it to deform if sufficiently high force was applied to the priming lever 8.

To avoid this potential problem, the cam member 72 is made to a form that varies its force versus distance profile along its length.

Figure 12:
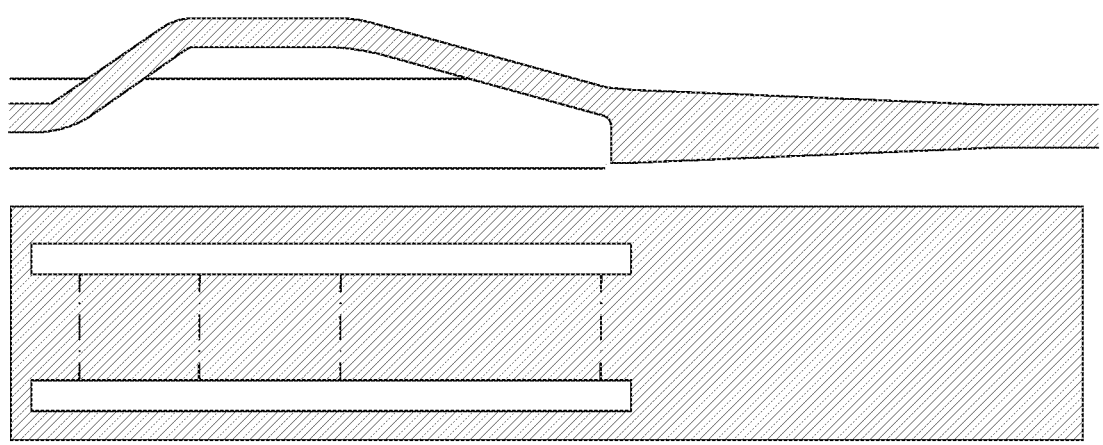
FIG. 12 illustrates schematically the preferred profile for the cam member.

An example of a suitable form is shown in FIG. 12. The preferred embodiment includes two such members arranged back to back. The solid wedge shape profile at the right hand side as illustrated in FIG. 12 has the same profile as shown in FIG. 11. This form rigidly transmits the force applied by the priming lever 8 to the insert 26. The length of this profile is chosen so that, for all devices, the prodgers 76 will be moved sufficiently far to break the foils 22, 24 by this profile. Once the foils 22, 24 are broken, much less force is required, but the distance that the insert 26 must move may vary from device to device. Thus, for the last part of its travel, the cam member 72 cross-section is designed to provide compliance in its movement. This ensures that the cam member 72 provides sufficient force for the insert 26 to be pushed to the end of its available travel in the anvil plate 32. However, after the insert 26 is stopped at the end of its travel, the force that the cam member 72 applies to the prodger 76 is limited to that generated as it deforms. This can be much less than the force that would be applied if the prodger 76 were rigidly connected to the priming member 60.

In this way, reliable opening of the pocket is achieved using components that can be manufactured using conventional materials and moulding processes.

The action of cam member 72 and prodger 76 is further illustrated in FIGS. 16(*a*) to 16(*h*). These Figures show the cam member 72 and prodger 76 at sequential positions as the priming lever 8 and priming member 60 are moved to open a pocket. The Figures are grouped in pairs, each group giving two views of the same position.

FIGS. 16(*a*) and 16(*b*) show the prodger 76*a* in its fully retracted position at one end of the cam member 72. The prodgers 76*a* and 76*b* are identical components that clip together with the cam member 72 between them. Each prodger 76 has features 86 at the ends of their arms 80 that locate with additional cam surfaces 88 formed on the priming member 60 either side of the elongate openings though which the arms 80 extend.

Where a prodger member 76 has penetrated past the first surface of a carrier disc in order to push the pocket through the second surface, then it is necessary to retract the prodger member 76 before the carrier disc can be indexed to its next position.

A spring could be used to achieve this if it were positioned to press the prodger member 76 against its base surface. However, it is preferable to have an active method for retracting the prodger member 76 that acts as the cam member 72 is returned to the original position. However, where the action of returning the cam member 72 to its original position is also used to index the carrier disc, it is important to ensure that the retraction of the prodger members 76 is completed before the carrier disc is indexed.

A preferred method of achieving this is by the use of the further cam surfaces 88 located in the non-moving housing in which the cam member and carrier discs are located.

Figure 17A:
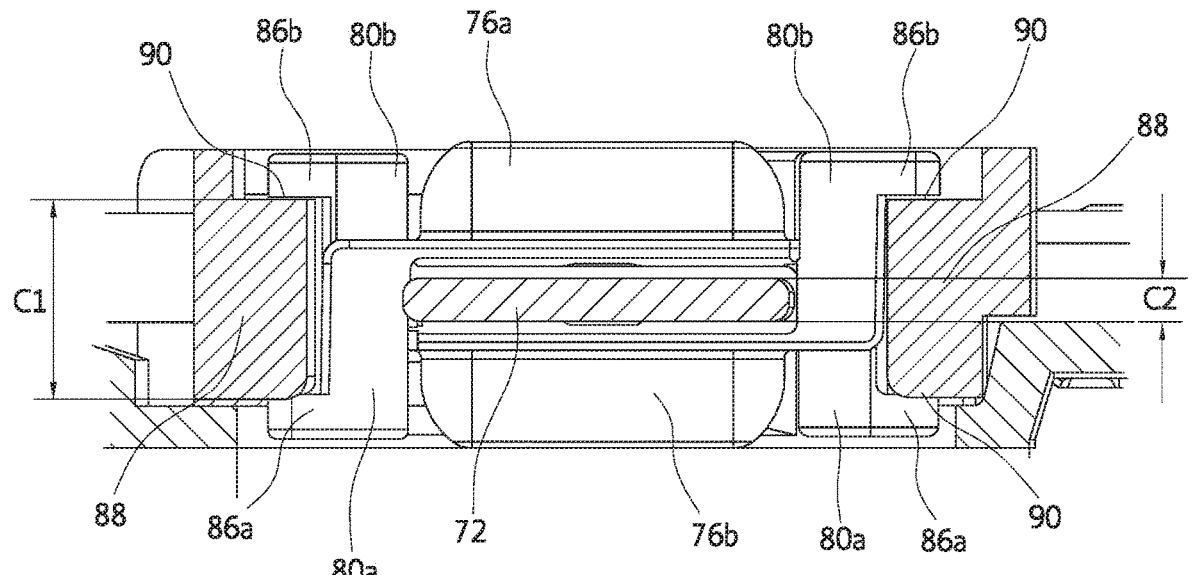
FIGS. 17(a) and (b) illustrate cross-sections through the components of FIGS. 16(a) to (h)
Figure 17B:
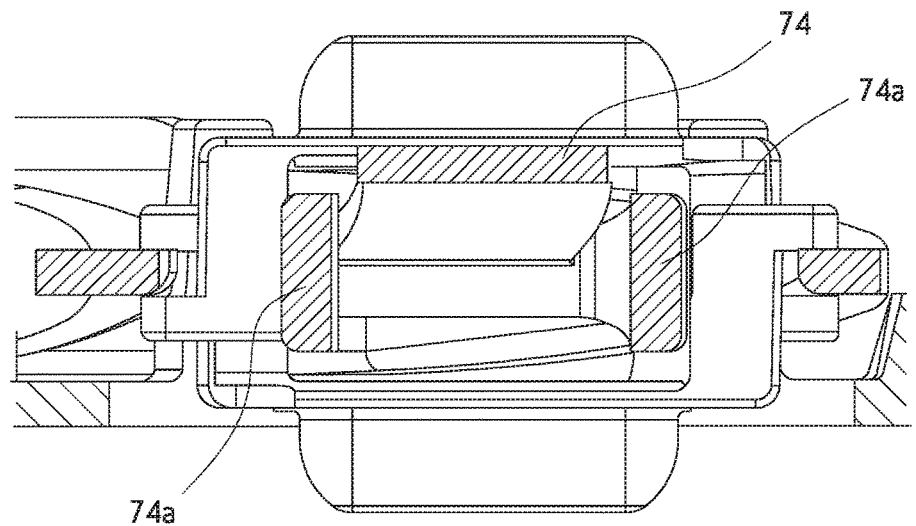
Figure 18:
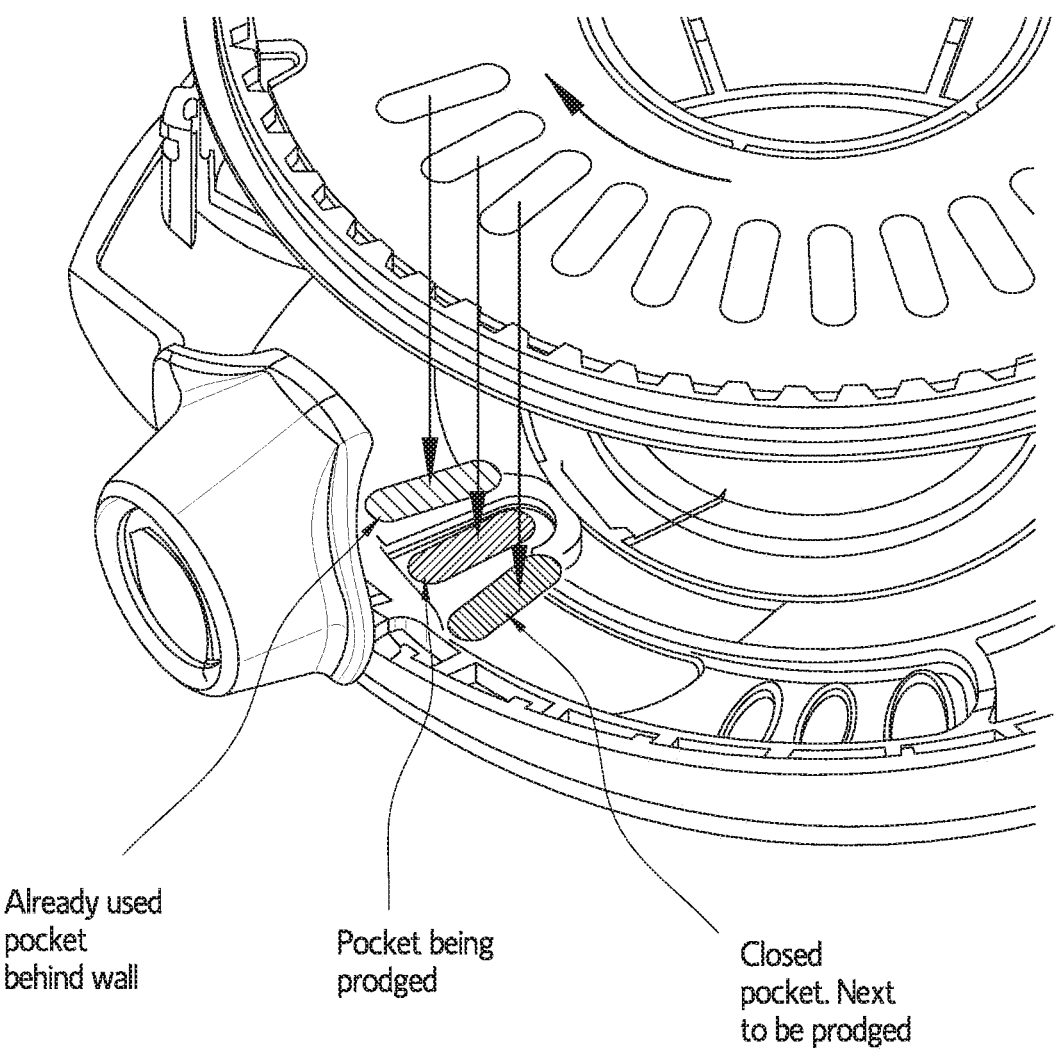
FIG. 18 illustrates pockets being opened in a device embodying the present invention.

FIG. 17(*a*) shows a schematic cross section through the prodgers 76*a* and 76*b* also in their retracted position.

The location of prodger 76*a* is constrained by the surface 90 of the cam 88 and the cam surface 74 of the cam member 72. The cams 88 and cam member 72 are designed so that their thickness CI and C2 change along the direction of the primary member 60 motion. FIG. 17(*b*) shows the prodgers 76*a* and 76*b* in their open position where it can be seen that C2 has increased and CI decreased compared to their values at the closed position.

The cam member 72 has a rectangular cross section C2 at one end that gradually increases in area. At the point that it starts to become a compliant wedge, rather than a rigid one, the wedge splits into a central part that pushes up 74 and two side parts that push down 74*a*.

This arrangement provides a positive force to both open and close the prodgers 76*a* and 76*b*.

FIGS. 16(*c*) to 16(*h*) show how the concept illustrated in FIGS. 17(*a*) and (*b*) might be implemented.

FIGS. 16(*c*) and (*d*) show the prodgers 76*a* and 76*b* where the cam member 72 has completed approximately one third of its full travel. The cam member 72 over this section is of uniform thickness such that the prodgers are fully retracted. This allows the movement of the rotary priming member 60 on the return stroke over this section to drive the indexing mechanism (as will be described below).

FIGS. 16(*e*) and (*f*) show the prodgers 76*a* and 76*b* where the cam member 72 has completed two thirds of its travel. The cam member 72 along this section includes the circumferential grooves 84 mentioned above. The raised parts of the cam member 72 are sufficient to rigidly couple the force applied to the priming lever 8 to the prodgers 76*a* and 76*b* and the grooves 84 are provided solely to increase the tolerance of the mechanism to stray powder that may have collected on the cam surface 74.

FIGS. 16(*g*) and (*h*) show the prodger where the cam member 72 has completed its travel. In this section, the cam member 72 is not solid but split into a central section and two side sections arranged so that the central section presses up against one prodger whilst the two outer sections press down against the other prodger.

If the prodgers 76*a* and 76*b* reach the end of their travel before the cam member 72 reaches the end of its travel, then the thinned section of the cam member 72 at this point will be deflected, thereby limiting the force applied to the prodgers 76*a* and 76*b* over the remaining travel of the cam member 72.

In the preferred embodiment, the indexing of the two carrier assemblies (FIGS. 5(*a*) and (*b*)) is accomplished by an indexing mechanism that causes a carrier 12 to be incremented by one pocket each time the priming lever 8 is actuated and a changeover mechanism that causes the indexing mechanism initially to drive the first carrier 12 but, when the last pocket of that carrier 12 has been used, for that carrier 12 to remain stationery whilst the second carrier 12 is incremented when the indexing mechanism is actuated.

The preferred indexing mechanism illustrated in FIGS. 14(a) to (f) uses a 3 peg Geneva 100 that rotates exactly 120° each time the indexing mechanism is actuated. The Geneva peg wheel 100 has two gears co-axial with the peg-wheel arranged so that the gears can engage with teeth 35 on the airway plates 34.

To avoid having both airway plates 34 driven simultaneously, it is arranged that, at one location around the airway plate 34, the gear teeth 35 are missing. As a result, at this location, rotation of the Geneva peg wheel 100 does not rotate the airway plate 34. Thus, the indexing mechanism drives the first carrier 12 via the Geneva 100 and its gears until it reaches the end of the gear teeth 35 for that carrier 12. The next indexing moves the first carrier 12 to its non-driven position, i.e. where the gear teeth 35 are missing, and engages a changeover mechanism which rotates the second carrier 12 until its gears 35 are engaged with the gears on the Geneva peg wheel 100.

A preferred embodiment of the indexing mechanism is illustrated in FIGS. 14(a) to 14(f). In these, it can be seen that the peg wheel 100 is located with its axis parallel t0 the axis of the dose carriers 12 and rotary priming member 60.

The rotary priming member 60 incorporates many of the functional elements described previously within a single moulded component. It includes the priming lever 8, the cam member 72 and the prodger closing cams 83, as well as being the driving member for the indexing Geneva 100.

The Figures start with the priming member 60 at the end of its travel where a pocket has been opened and shows what happens as the priming lever 8 is returned to its start position by the closing of the mouthpiece cover 4.

The peg wheel 100 has six pegs 102a-102c, 103a-103c arranged at 60° intervals around its edge. Three of these pegs 102a, 102b, 102c are longer than the other three 103 a, 103b, 103 c and are shown with black ends for clarity. As the rotary priming member 60 moves from its position in FIG. 14(a) to that in FIG. 14(b), the leading part 101 of a driving member 104 formed by the priming member 60 passes over the short peg 103 a with its periphery touching the edges of the longer pegs 102a and 102c preventing the peg wheel 100 from rotating. At the position shown in FIG. 14(b), a ratchet 105, which slopes downward and forward from the driving member 104, engages with the peg 103 a. As the priming member 60 and the driving member 104 continue to move from the position of FIG. 14(b) to that of FIG. 14(c), the peg wheel 100 is driven around. To permit the peg wheel 100 to rotate, a slot 106 is cut into the driving member 104 of the priming member 60 into which the long peg 102c can enter. At the position of FIG. 14(c), the ratchet 105 is starting to disengage with the peg 103 a but the trailing edge 107 of the slot 106 now engages with the long peg 102c and continues to drive the peg wheel 100 around through to the position shown in FIG. 14(d). At the position of FIG. 14(d), the edge 108 of the driving member 104 passes over the short peg 103 c. The peg wheel 100 then continues to rotate to the position of FIG. 14(e) to complete the forward motion of the peg wheel 100. The slot 109 is provided to accommodate the long peg 102b. At this position, the dose carrier 12 has been driven so that the next pocket to be opened is beyond its desired location and the mouthpiece cover 4 that has been driving the rotary priming member 60 is fully closed.

Figure 14A:
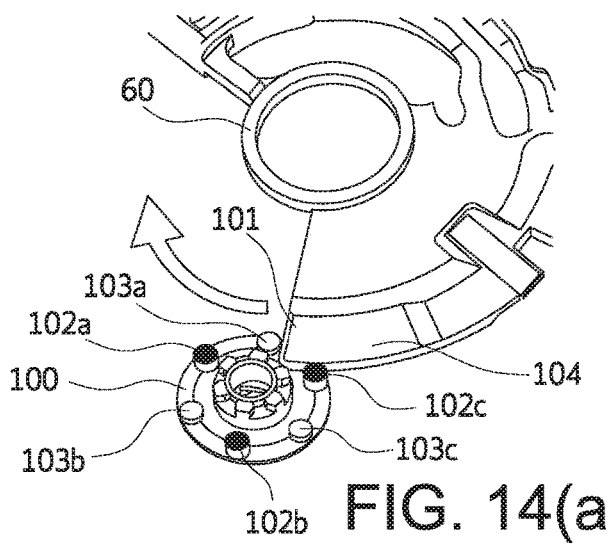
FIGS. 14(a) to (f) illustrate the Geneva mechanism of the indexing mechanism of an embodiment of the present invention.
Figure 14B:
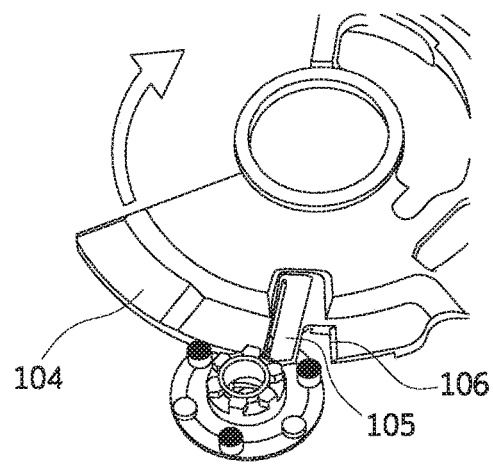
Figure 14C:
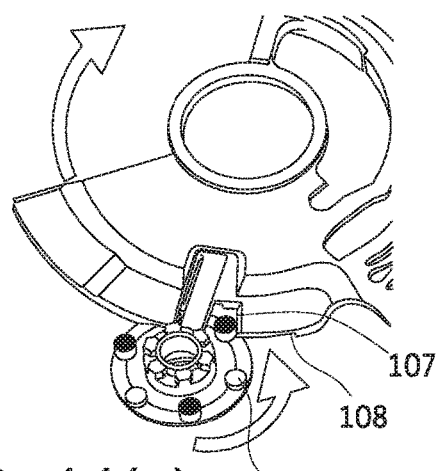
Figure 14D:
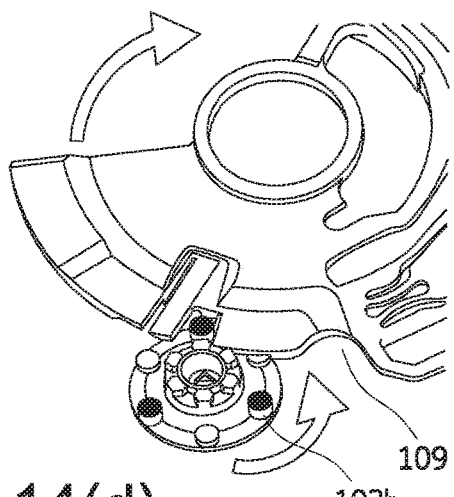
Figure 14E:
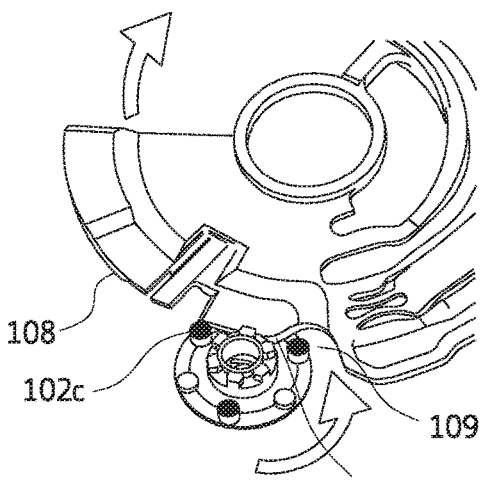

When the priming lever 8 is pushed in the reverse direction by the user to open a pocket, the initial part of the travel, over which the prodgers 76a and 76b are not moved, takes the rotary priming member 60 plate back from the position shown in FIG. 14(e) to that shown in FIG. 14(b). The angled face 110 in the slot 109 on the rotary priming member 60 pushes on the long peg 102b causing the peg wheel 100 to rotate backwards until the two long pegs 102b and 102c are both dis-engaged from the driving edges and pressing against the outer periphery 108 of the rotary priming member 60.

Figure 14F:
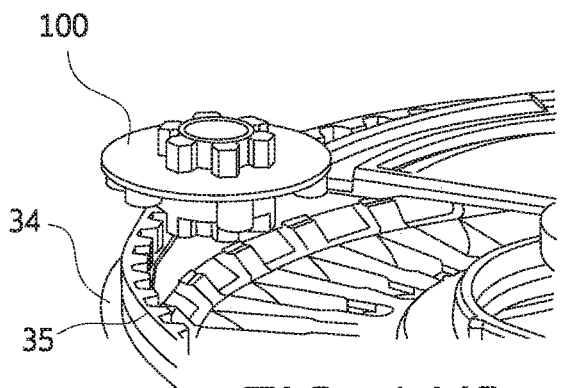

This accurately defines the rotary position of the peg wheel 100, ensuring that the prodgers 76a and 76b accurately line up with the pockets. The short peg 103c, that is within the outer periphery of the rotary priming member 60, is short enough to allow the ratchet 105 to return over the top of it. Thus, after the initial movement, the peg wheel 100 is held stationary throughout the remainder of the stroke opening a pocket. Thus, each indexing operation causes the peg wheel 100 to rotate 120°. The gears above and below the plane of the peg wheel 100 are shown in FIG. 14(f) which for clarity is viewed from the opposite side from FIG. 14(a) to 14(e). FIG. 14(f) shows the gears 35 on one of the airway plates 34 engaged with the gear on the peg wheel 100. The number of gear teeth on the airway plates 34 and peg wheel 100 are arranged so that the 120° motion of the peg wheel 100 increments the dose carrier plate exactly one pocket pitch.

The arrangement described here is advantageous in achieving precise intermittent motion control of two disks within very tight space allocation and with a minimal number of components.

As described previously, for the device to operate with two disk carrier plates, a changeover mechanism is preferably provided to cause the indexing mechanism initially to drive a first disk and, when this has had all of its pockets opened, to then drive a second disk. Such a changeover mechanism will be described with reference to FIG. 15(a) to FIG. 15(e). These Figures show the device viewed edge on with the two airway plates 34 arranged horizontally.

Figure 15A:
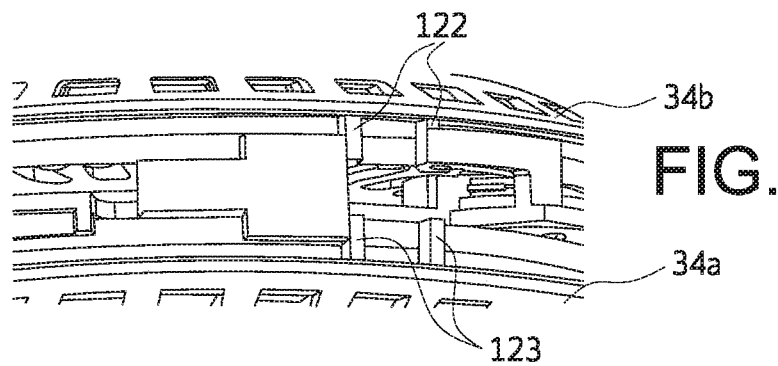
FIGS. 15(a) to (e) illustrate the changeover mechanism of an embodiment of the present invention.
Figure 15B:
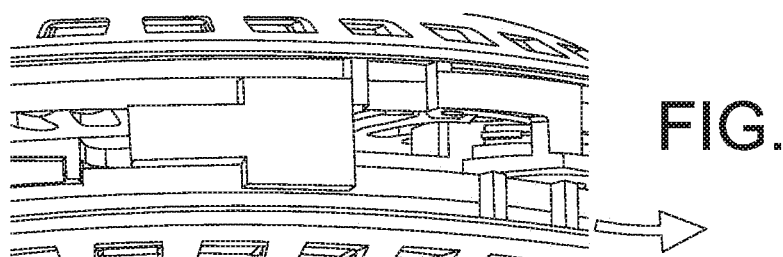

FIG. 15(a) shows the device in its position before a first pocket is opened.

In FIG. 1(b), airway plate 34a has been indexed by one position to the right. The two features 123 on the periphery of the airway plate 34a can be seen to have shifted.

Figure 15C:
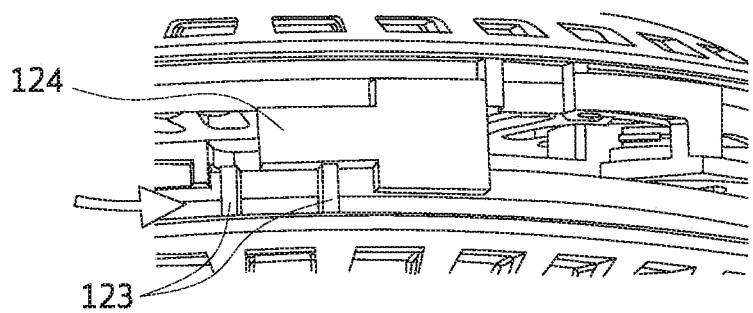
Figure 15D:
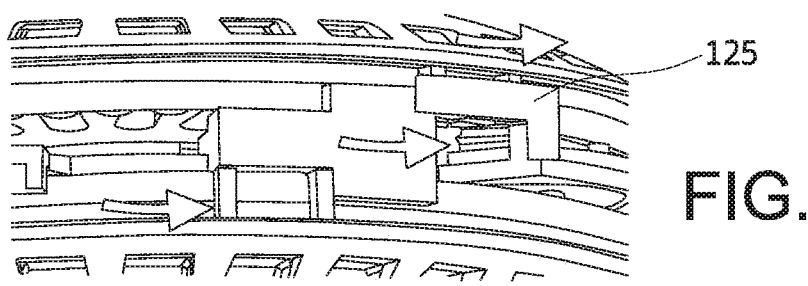
Figure 15E:
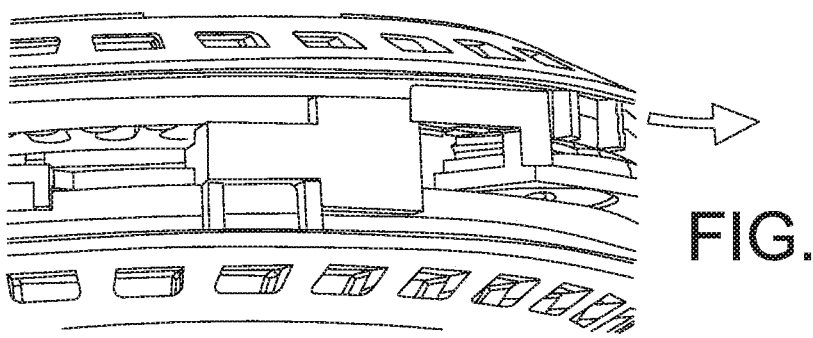
Figure 16A:
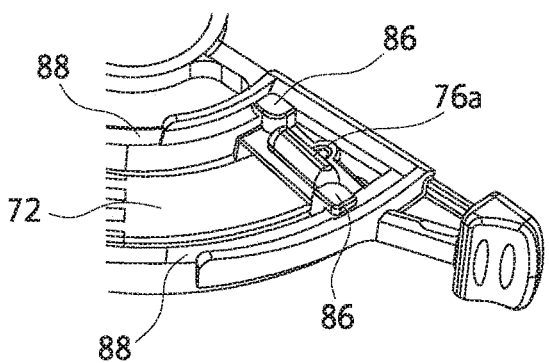
FIGS. 16(a) to (h) illustrate the dispensing mechanism of an embodiment of the present invention.
Figure 16B:
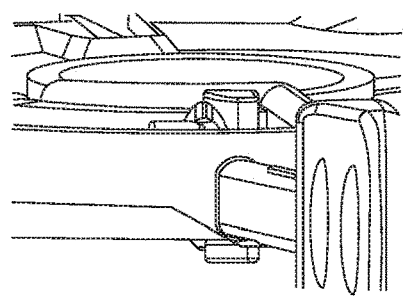
Figure 16C:
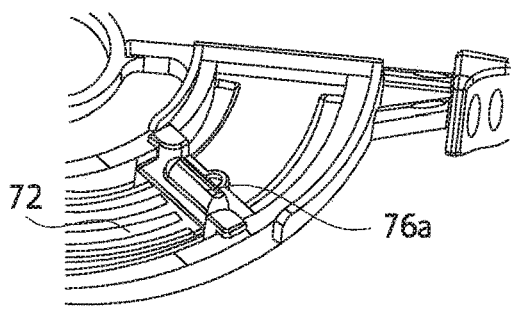
Figure 16D:
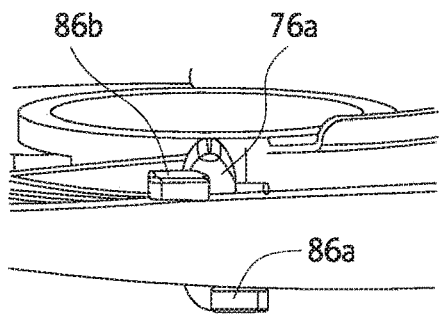
Figure 16E:
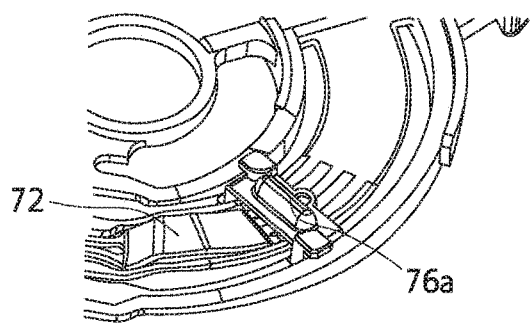
Figure 16F:
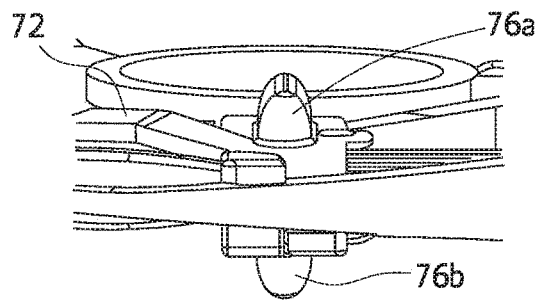
Figure 16G:
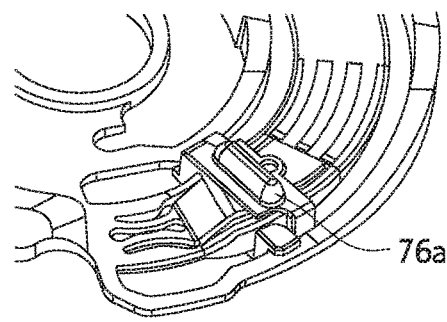
Figure 16H:
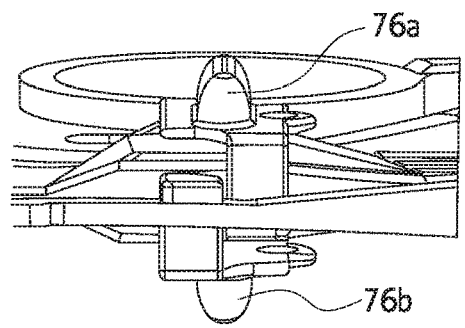

FIG. 15(c) shows the position after the last pocket of the lower carrier 12 of airway plate 34a has been opened. The rotation has brought the features 123 right around the device to the position shown. The next indexing operation causes the lower airway plate 34a to move as before.

However, the leading feature 123 pushes on a changeover component 124 which pushes on the feature 122 on the upper airway plate 34b causing both plates 34a and 34b and carriers 12 to move together. When the upper airway plate 34b was in its original position, the prodger 76b was aligned to the missing pocket part 82 providing a hard surface against which that prodger 76b could push whilst the other prodger 76a pushed against a pocket of the lower airway plate 34a. In addition, at this location, the missing teeth on the gear 35 of the upper airway plate 34b aligned with the gear on the Geneva peg wheel 100 and, hence, rotation j of the peg wheel 100 did not index the upper airway plate 34b. However, the indexing operation performed by the changeover component 124 on the upper airway plate 34b moves the gear of the upper airway plate 34b to engage with the gear of the peg wheel 100 and aligns the first pocket of the upper carrier 12 with the prodgers 76. Simultaneously, indexing by the priming member 60 causes the lower airway plate 34a to continue to move to a position which the gear teeth 35 on the lower airway plate 34a disengage from the gear on the peg wheel 100. The priming member 60 and peg wheel 100 move the lower airway plate 34a to a position in which the missing teeth on the gear 35 of the lower airway plate 34a are aligned with the gear on the Geneva peg wheel 100 and the missing pocket segment 82 of the lower dose carrier 12 is aligned with the prodgers 76.

The clip 125 provides an interlock that prevents any frictional coupling from causing the upper airway plate 34b to move before the lower airway plate 34a has arrived at the correct location.

Thus, changeover from the indexing of one disc to the other is achieved automatically and with minimal number of components and in a very small space.

The indexing of the device, in addition to moving the next pocket into alignment with the prodgers 76, preferably actuates a dose counter that provides a visual indication to the user of the number of doses remaining. The operation of the dose indicator will be described with reference to FIGS. 19 and 20.

It is preferable that the device, when dispensing medicament, indicates to the user the number of doses remaining in the device.

It is preferable that such indication is easily readable and, as such, very small numbers indicating the remaining doses would be a disadvantage. Within the size constraints of a pocket portable device that contains 60 doses providing such a display is challenging.

The simplest arrangement of marking the carrier discs with numbers visible through windows in the casework requires, where two carrier discs are used, the user to view different windows and, in addition, the space available around the carrier disc means that the size of the numbers would be small.

A preferred method is to employ a display with separate units and tens indication, driven such that the tens display index one number as the unit display index from 9 to 0. This allows larger numbers to be used within the same casework. The two discs may be provided concentrically one within the other and preferably co axially with the axis of the device, for instance on the shaft 68 illustrated in FIG. 13. The displayed units and tens are visible through the window 10 illustrated in FIG. 1(a).

In a preferred embodiment, the display counts down to zero, but the tens disc is not provided with a "0". Instead, it is provided with an indicator, for instance a symbol, colour light etc to indicate to the user that the device is nearing the end of its functional life.

The preferred embodiment uses another Geneva and gear arrangement that is driven from the movement of the carrier discs. It is preferable that a single counter is increment initially by the motion of the first carrier disc and subsequently by the motion of the second carrier disc such that the fact that the device contains two carrier discs is not apparent to the user.

Figure 20A:
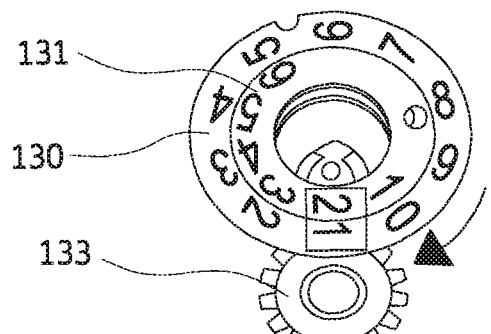
FIGS. 20(a) to (e) illustrate operation of the counter of FIGS. 19(a) to (d)

FIG. 20(a) shows a view of the dose counter display. The counter consists of two concentric rings 130, 131 with numbers formed in the rings facing toward the outer casing 2 of the device. The outer ring is the units counter 130 and the inner ring is the tens counter 131. The window 10 is provided in the outer casework 2 is arranged to permit the user to see only one digit of the units counter 130 and the adjacent digit of the tens counter 131. In FIG. 20(a), the counter indicates that there are 21 doses left. The operation of the counter requires the units counter 130 to index by 36° every time the indexing mechanism is actuated and for the tens counter to index by 36° only as the units counter moves from displaying 9 to 0. It can be seen that the units digits are evenly distributed around the ring whereas, for the example shown in FIG. 20(a) which has 60 doses, there are only the digits 1 to 6 on the tens counter 131.

The counter is driven by a gear 133 which itself is driven by one of the gears on the indexing Geneva peg wheel 100. In the preferred embodiment described above, the indexing Geneva 100 turns through 120° for each indexing operation and the gear on it has six teeth. The gear 133 has fifteen teeth and engages with the twenty teeth 134 of the units counter illustrated in FIG. 19(a). Thus, the 120° rotation of the indexing Geneva 100 drives the units counter 130 through 36°. FIG. 19(a) shows the units counter ring 130 viewed from behind the face on which the numbers are formed.

A counter Geneva wheel 135 is shown located inside the units counter ring 130 for mounting on a fixed post which is part of chassis 66.

An actuated peg 136 for the counter Geneva mechanism is located on the inner diameter of the units counter wheel 130. This peg 136 engages with one of the three indentations 137 in the Geneva wheel 135 causing the Geneva wheel 135 to rotate by 120° as the peg 136 passes by the wheel 135 during its 36° rotation between displaying the digits 9 and 0.

It should be noted that in this Geneva mechanism, the peg 136 is on the outer larger diameter component 130 and this drives the slotted smaller wheel 135 whereas, for the indexing Geneva 100, the slots are on the larger wheel and they drive the pegs on the smaller wheel. However, both are examples of a Geneva type mechanism providing intermittent rotation with accurate location between the rotations.

The Geneva wheel includes cam faces 138 which contact against the inner wall 139 of the units counter 130 preventing the Geneva 135 rotating between indexing. To permit the Geneva 135 to rotate as it is pushed by the peg 136, there is a gap 139a in the inner wall 139 adjacent to the peg 136.

The Geneva has a 3 tooth gear on its underside engaging with pegs on the tens counter ring to drive it.

FIG. 19(a) through to FIG. 19(e) show the positions of the Geneva wheel 135, the drive gear 133 and the units counter 130 at four stages during the 36° rotation of the units counter.

Figure 20B:
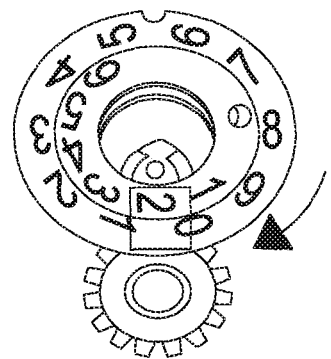
Figure 20C:
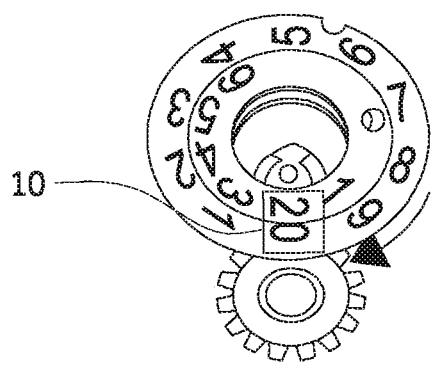
Figure 20D:
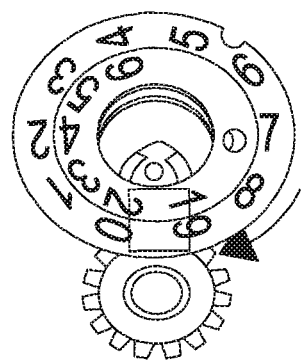
Figure 20E:
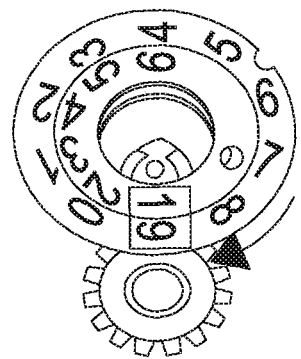
Figure 21A:
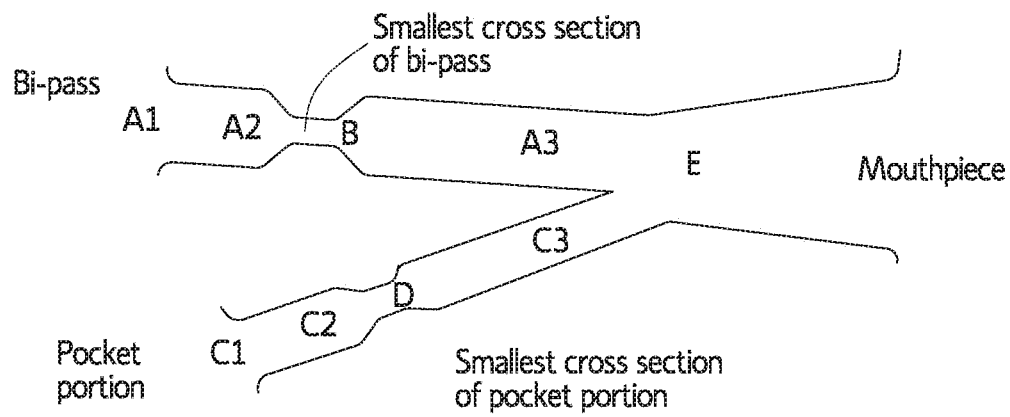
FIGS. 21(a) and (b) illustrate preferred cross sectional areas at various locations in an embodiment of the present invention.
Figure 21B:
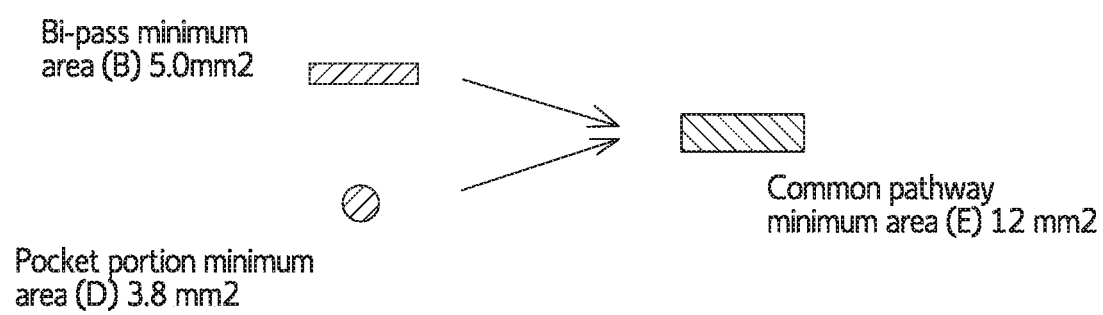

FIG. 20(a) to FIG. 20(c) show the motion of the two counter wheels as they index from 21 doses to 20 doses remaining, when only the outer units counter 130 moves. FIG. 20(c) to FIG. 20(e) show the corresponding situation from 20 to 19 doses remaining where both counters index.

After the last dose has been used, the remaining doses display will read 0 indicating that the device is empty to the user.

However, if the user does not look at the display, they may actuate the device again when desiring further doses.

It is preferable that the device provides some positive feedback to the user, as it is being actuated, that it is empty. This feedback can be in the form that the priming lever 8 cannot be moved to its operating position with the level of force normally used. This tactile feedback provides a lock-out feature.

A preferred method of achieving this with the two disc device is to arrange that after the last dose has been used, the second disc indexes such that it has no pocket under the prodger. At this point, the two prodger members 76 both face surfaces of the discs without pockets. Thus as the priming lever 8 is moved, neither prodger member 76 can move onto a disc and the resulting force on the prodger members 76 is transmitted back through the drive mechanism to the priming lever 8 and hence to the user.

Whilst the user may be able to apply sufficient force to move the priming lever 8 through to its home position, this will only be possible by forcing the discs to separate against the constraint of the casework. The force required to do this can be made sufficiently greater that the normal actuation force as to be obvious to the user.

From the description, it can be seen that this mechanism provides a clear visual indication of the number of doses remaining with a minimal number of components.

The preferred embodiment described above is arranged consecutively to dispense the powder from each pocket of one carrier and then subsequently the powder from each pocket of the other carrier. However, it should be appreciated that it is also possible for a device to dispense powder from pockets alternately from one carrier and then the other carrier. Alternatively, pockets of both disks may be dispensed simultaneously.

By dispensing powder from both carriers, either one after the other or simultaneously, it is possible for the user to inhale the powder from both carriers simultaneously. This arrangement is particularly advantageous when used with disks containing different medicament. In particular, it is preferred to provide disks containing a combination of medicaments that are more effective together than singularly. By way of example, a steroid compound could be dispensed from one disk and a long acting beta agonist (LABA) from the other disk for the treatment of, for example, asthma or chronic obstructive pulmonary disease. Examples of long acting beta agonists include formoterol and salmeterol and examples of steroids include fluticasone propionate. budesonide and monetasone furoate.

It is also possible to adapt the mechanism so to as to arrange for selective dispensing from one or both carriers. Where both disks are provided with the same medicament, this may be used to vary the dispensed dosage.

Although a device has been described with reference to a particular type of carrier, in particular having through holes and sealed with lidding sheets on either side, it is also possible to use other carriers, such as more conventional blister packs. These could include inserts similar to those described above. However, alternatively, powder in the pockets themselves could outwardly burst the lidding sheet. Also certain aspects of the device are applicable with other opening arrangements such as peeling or cutting of the lidding sheet.

Finally, it should be appreciated that the device can be provided with carriers pre-installed or, alternatively, ready for use with appropriate carriers.

As illustrated in FIG. 13, the preferred arrangement described above can be provided conveniently as three assemblies for use with carriers 12. In particular, a first cover sub-assembly A receives one carrier 12 and a second cover sub-assembly B receives another carrier 12. The two cover sub-assemblies A and B are then secured to one another with a chassis sub-assembly C therebetween.

What is claimed is:

1. A device for dispensing powdered medicaments, comprising at least one carrier bearing a plurality of respective pockets, each pocket holding a dose of a powdered medicament; a mouthpiece through which to inhale an airstream carrying the dose of the powdered medicament from an opened pocket of the plurality of respective pockets; an indexing mechanism for indexing the at least one carrier between the respective pockets, from a storage position to a discharge position; a first counter ring having a first display surface displaying numbers on the first display surface, the first counter ring being rotatable about a counter axis; and a second counter ring having a second display surface indicating tens counts, the second counter ring being rotatable about the counter axis; the first counter ring being driven with the indexing mechanism, the second counter ring being positioned within the first counter ring, wherein the first display surface and the second display surface are planar and perpendicular to the counter axis.

2. The device according to claim 1, wherein the at least one carrier comprises a first carrier and a second carrier, and the indexing mechanism is configured to index each of the first carrier and the second carrier between respective pockets thereof.

3. The device according to claim 2, wherein the first carrier and the second carrier are indexed such that respective doses of powdered medicament are dispensed from each of the first and second carriers simultaneously.

4. The device according to claim 3, wherein, when the device is indexed, one pocket from the first carrier and one pocket from the second carrier are opened together.

5. The device according to claim 2, wherein the first carrier and the second carrier are indexed such that respective doses of powered medicament are dispensed from each of the first and second carriers sequentially, one at a time in an alternating fashion.

6. The device according to claim 2, wherein the first carrier and the second carrier are arranged side by side; the device comprises a housing and a priming lever extending out of the housing; the priming lever is configured to rotate about a central axis of the device; and the priming lever extends from between the first carrier and the second carrier.

7. The device according to claim 2, wherein the plurality of respective pockets of the first carrier carries a different powered medicament than the plurality of respective pockets of the second carrier.

8. The device according to claim 7, wherein the powdered medicament carried by the first carrier and the powdered medicament carried by the second carrier comprise two different medicaments that are more effective for treating asthma and/or chronic obstructive pulmonary disease together than singularly.

9. The device according to claim 1 wherein, when the device is indexed, only one of the plurality of respective pockets of the at least one carrier is opened each time the device is indexed.

10. The device according to claim 1 wherein, when the device is indexed, two of the plurality of respective pockets of the at least one carrier are opened together.

11. The device according to claim 1, wherein the device comprises a housing and a mouthpiece cover, and the mouthpiece cover is formed as a separate component from the housing, the mouthpiece cover being configured to be rotated relative to the housing to expose the mouthpiece.

12. The device according to claim 1, wherein the device comprises a housing and a priming lever extending out of the housing, and the priming lever is configured to rotate about a central axis of the device.

13. The device according to claim 12, wherein the priming lever has a first position and a second position such that a movement from the first position to the second position is arranged to prime the device, and priming the device comprises exposing at least one dose of powdered medicament carried by the at least one carrier.

14. The device according to claim 13, wherein the priming lever is adjacent to the mouthpiece at the first position.

15. The device according to claim 12, wherein a movement of the priming lever operates the indexing mechanism to index the device such that at least one unused and unopened pocket of powdered medicament is moved into a position for dispensing and is opened.

16. The device according to claim 15, wherein the device comprises a mouthpiece cover, wherein rotation of the mouthpiece cover from an open position to a closed position returns the priming lever to the first position and covers the mouthpiece.

17. The device according to claim 15, wherein when a pocket is opened but the dose of powdered medicament held therein is not inhaled, a further movement of the priming lever indexes the open pocket to a position where the powder released therefrom is held within the device.

18. The device according to claim 15, wherein each of the plurality of respective pockets is sealed by a foil, and a rupturing of the foil during indexing of the device imparts a resistance on the priming lever and thus provides tactile feedback to the user.

19. The device according to claim 18, wherein when the priming lever is rotated, the force required to continue rotating the priming lever is increased due to resistance of the foil until such time as the foil is ruptured, whereupon the force required to rotate the priming lever is reduced.

20. The device according to claim 1, wherein the at least one carrier comprises at least one disc, the at least one disc bearing a plurality of respective pockets.

21. The device according to claim 1, wherein the at least one carrier comprises at least one blister-pack array, the at least one blister-pack array bearing a plurality of respective pockets.

22. The device according to claim 1, wherein each of the plurality of respective pockets is sealed by a lidding sheet.

23. The device according to claim 22, wherein each respective dose of the powdered medicament is exposed by a peeling of the lidding sheet.

24. The device according to claim 22, wherein the lidding sheet is ruptured as a consequence of moving a pocket from a respective storage position to a respective discharge position.

25. The device according to claim 1, wherein the powdered medicament comprises at least one of a long acting beta-agonist, a steroid, or any combination thereof.

26. The device according to claim 1, wherein the powdered medicament comprises at least one of formoterol, salmeterol, fluticasone, budesonide, monetasone, or any combination thereof.

27. The device according to claim 1, further comprising an intermittent-motion mechanism for driving the second counter ring from the first counter ring.

28. The device according to claim 27, wherein the second counter ring rotates between consecutive tens counts when the first counter ring rotates between two predetermined consecutive unit counts.

29. The device according to claim 27, wherein the intermittent-motion mechanism is a Geneva mechanism.

30. The device according to claim 27, further comprising a counter gear engaged with a first gear of the first counter ring, wherein the intermittent-motion mechanism comprises a second gear, and wherein rotation of the counter gear is configured to rotate the first counter ring, with the first counter ring configured to rotate the second counter ring.

31. The device according to claim 30, wherein the first counter ring comprises a peg configured to rotate the second gear, and wherein the peg is positioned on an inner diameter of the first counter ring.

32. The device according to claim 1, wherein the first counter ring includes a pin for engaging a Geneva wheel rotatable about an axis offset from the counter axis and the second counter ring includes features engageable by the Geneva wheel.

33. The device according to claim 1, wherein the first counter ring and the second counter ring rotate about an axis parallel to the axis of the dose carriers.

34. The device according to claim 1, further comprising walls defining at least one first flow path for deaggregating the powdered medicament from an open pocket in the discharge position and at least a second flow path which bypasses the open pocket.

35. The device according to claim 34, wherein the walls defining the first flow path are configured to force the airstream to change direction such that the dose of powder in the airstream is deaggregated.

36. The device according to claim 35, wherein the walls defining the first flow path have rounded corners configured to limit a pressure drop such that the pressure drop does not exceed 4 kPa at 60 I/min.

37. The device according to claim 34, wherein each of the at least one first flow path comprises a section of relatively reduced cross-sectional area oriented so as to be directed towards an open pocket in the discharge position and configured to direct a relatively high velocity airstream into the pocket.

38. The device according to claim 37, wherein the section of relatively reduced cross-sectional area of each of the at least one first flow path is between 50% and 60% of the cross-sectional area of the smallest part of the second flow path.

39. The device according to claim 37, wherein the section of relatively reduced cross-sectional area of each of the at least one first flow path is between 2.0 mm$^2$ and 10.0 mm$^2$.

40. The device according to claim 1, wherein the second display surface comprises an indicia indicating that the device is nearing the end of its functional life, and the indicia is displayed when a predetermined number of doses remain within the device.

41. The device according to claim 40, wherein the indicia comprises a symbol, a color, a light, or any combination thereof.

42. The device according to claim 40, wherein the indicia is not a number "0".

43. The device according to claim 1, wherein the indexing mechanism comprises a wheel and a plurality of gears, and wherein, upon rotation of the wheel and the plurality of gears, the at least one carrier is indexed between the respective pockets.

44. The device according to claim 43, further comprising a counter gear engaged with a first gear of the first counter ring, wherein, upon rotation of a first gear of the plurality of gears of the indexing mechanism, the counter gear rotates to drive the first counter ring.

45. The device according to claim 43, wherein the indexing mechanism comprises a ratchet.

46. A device for dispensing powdered medicaments, comprising
   a first carrier bearing a plurality of respective pockets and a second carrier bearing a plurality of respective pockets, each pocket of the first and second carriers holding a dose of a powdered medicament;
   a mouthpiece through which to inhale an airstream carrying the dose of the powdered medicament from an opened pocket of the plurality of respective pockets;
   an indexing mechanism for indexing the at least one carrier between the respective pockets, from a storage position to a discharge position, the indexing mechanism being configured to index each of the first carrier and the second carrier between respective pockets thereof;
a first counter ring having a first display surface displaying numbers on the first display surface, the first counter ring being rotatable about a counter axis;
a second counter ring having a second display surface indicating tens counts, the second counter ring being rotatable about the counter axis; the first counter ring being driven with the indexing mechanism, the second counter ring being positioned within the first counter ring, the first display surface and the second display surface being planar and perpendicular to the counter axis;
a housing enclosing the at least one carrier; and
a priming lever extending out of the housing, the priming lever being configured to rotate about an axis of the device, the priming lever having a first position and a second position such that a movement from the first position to the second position is arranged to prime the device,
wherein priming the device comprises exposing at least one dose of powdered medicament carried by the at least one carrier; and a movement of the priming lever operates the indexing mechanism to index the device such that two unused and unopened pockets of powdered medicament, one from the first carrier and one from the second carrier, are moved into a position for dispensing and are opened.

47. The device according to claim 46, wherein the indexing mechanism comprises a wheel and a plurality of gears, and wherein, upon rotation of the wheel and the plurality of gears, the first carrier and the second carrier are indexed between the respective pockets.

48. The device according to claim 47, further comprising a counter gear engaged with a first gear of the first counter ring, wherein, upon rotation of a first gear of the plurality of gears of the indexing mechanism, the counter gear rotates to drive the first counter ring.

49. The device according to claim 47, wherein the indexing mechanism comprises a ratchet.

50. A device for dispensing powdered medicaments, comprising
at least one carrier bearing a plurality of respective pockets, each pocket holding a dose of a powdered medicament;
a mouthpiece through which to inhale an airstream carrying the dose of the powdered medicament from an opened pocket of the plurality of respective pockets;
an indexing mechanism for indexing the at least one carrier between the respective pockets, from a storage position to a discharge position;
a first counter ring having a first display surface displaying numbers on the first display surface, the first counter ring being rotatable about a counter axis; and
a second counter ring having a second display surface indicating tens counts, the second counter ring being rotatable about the counter axis; the first counter ring being driven with the indexing mechanism, the second counter ring being positioned within the first counter ring, the first display surface and the second display surface being planar and perpendicular to the counter axis;
a housing enclosing the at least one carrier;
a mouthpiece cover formed as a separate component from the housing, the mouthpiece cover being configured to be rotated relative to the housing to expose the mouthpiece; and
a priming lever extending out of the housing, the priming lever being configured to rotate about an axis of the device, the priming lever having a first position and a second position such that a movement from the first position to the second position is arranged to prime the device, wherein priming the device comprises exposing at least one dose of powdered medicament carried by the at least one carrier; and a movement of the priming lever operates the indexing mechanism to index the device such that at least one unused and unopened pocket of powdered medicament is moved into a position for dispensing and is opened.

51. The device according to claim 50, wherein the indexing mechanism comprises a wheel and a plurality of gears, and wherein, upon rotation of the wheel and the plurality of gears, the at least one carrier is indexed between the respective pockets.

52. The device according to claim 51, further comprising a counter gear engaged with a first gear of the first counter ring, wherein, upon rotation of a first gear of the plurality of gears of the indexing mechanism, the counter gear rotates to drive the first counter ring.

53. The device according to claim 51, wherein the indexing mechanism comprises a ratchet.

\* \* \* \* \*